United States Patent
Bhat et al.

(10) Patent No.: US 9,856,232 B1
(45) Date of Patent: Jan. 2, 2018

(54) DIHYDROPYRIMIDINONE DERIVATIVES

(71) Applicant: KING SAUD UNIVERSITY, Riyadh (SA)

(72) Inventors: Mashooq Ahmad Bhat, Riyadh (SA); Mohamed Abdulrahman Al-Omar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/628,476

(22) Filed: Jun. 20, 2017

(51) Int. Cl.
| | |
|---|---|
| C07D 401/02 | (2006.01) |
| C07D 239/10 | (2006.01) |
| C07D 273/02 | (2006.01) |
| C07D 227/02 | (2006.01) |
| C07D 221/00 | (2006.01) |
| A61K 31/505 | (2006.01) |

(52) U.S. Cl.
CPC .......... *C07D 401/02* (2013.01); *A61K 31/505* (2013.01); *C07D 221/00* (2013.01); *C07D 227/02* (2013.01); *C07D 239/10* (2013.01); *C07D 273/02* (2013.01)

(58) Field of Classification Search
CPC .. C07D 401/02; C07D 239/10; C07D 273/02; C07D 227/02; C07D 221/00; A61K 31/505
See application file for complete search history.

(56) References Cited

U.S. PATENT DOCUMENTS

| | | | |
|---|---|---|---|
| 7,687,510 B2 | 3/2010 | Gielen-Haertwig et al. | |
| 9,115,093 B2 | 8/2015 | Gnamm et al. | |
| 9,440,930 B2 | 9/2016 | Oost et al. | |
| 9,458,113 B2 | 10/2016 | Peters et al. | |
| 2011/0034433 A1 | 2/2011 | Von Nussbaum et al. | |
| 2015/0239877 A1* | 8/2015 | Zhang .................. | C07D 417/04 514/235.8 |

FOREIGN PATENT DOCUMENTS

WO   WO 98/33791 A   8/1998

OTHER PUBLICATIONS

Beena K.P, R. Suresh, A. Rajasekaran, P. K. Manna Dihydropyrimidiriones—A Versatile Scaffold with Diverse Biological Activity, Journal of Pharmaceutical Sciences and Research, 2016, 8(8), 741-746.
Bhargava KP, Gupta MB, Tangri KK, Mechanism of ulcerogenic activity of indomethacin and oxyphenbutazone, Eur J Pharmocol, 1973, 22, 191-195.
Chiu PJS, Gerhart C, Brown AD, Barnett A, Effects of gastric antisecretory cytoprotectant 2-methyl-8-(phenylmethoxy)imidazo (1,2 a)-pyridine-3-acetonitrile (Sch 28080) on cysteamine, reserpine and stress ulcers in rats, Arzneim Forsch, 1984, 34, 783.
C. Ivankov, O. Petkov, P. Petrov, M. Taskov, R. Athanassova, E. Tsvetkova, V. Kotsev, G. Lyutakov, G. Nikolov, E. Savov, Synthesis, Gastroprotective, Antisecretory and Anti-helicobacter Effect of N-[3-(3-1-Piperidinylmethyl) phenoxy)Propyl]-hydroxyacctamide 2-Hydroxypropane-1,2,3-tricarboxylate Bismuth (3+) Complex (MX1)-MC1, Jouranl of Pharmacy and Pharmacology, Mar. 1996, 48(3), pp. 297-301.
Kulbhushan Rana, Balbir Kaur, Gagandeep Chaudhary, Suresh Kumar, Sandeep Goyal, Synthesis and Anti-ulcer Activity of Some Dihydropyrimidimes, International Journal of Pharmaceutical Sciences and Drug Research, 2011, 3(3), pp. 226-229.
Venkateshwarlu Kodhati, Malla Reddy Vanga, Narsimha Reddy Yellu, Synthesis and Anti Bacterial and Anti-ulcer Evaluation of New S-mannich Bases of 4,6-diaryl-3,4-dihydropyrimidin-2(1H)-thiones, Journal of the Korean Chemical Society, 2013, 57(2), pp. 234-240, Republic of Korea.
Karber, G, Arch. Exptl. Pathol. Pharmakol, 1963, 162, 480-483.

* cited by examiner

*Primary Examiner* — Alexander R Pagano
*Assistant Examiner* — Ebenezer O Sackey
(74) *Attorney, Agent, or Firm* — Richard C. Litman

(57) ABSTRACT

A dihydropyrimidinone derivative includes a compound having a chemical structure according to Formula 1:

(Formula 1)

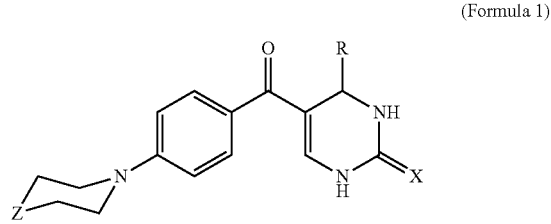

wherein
Z is selected from $CH_2O$, O, and N;
X is selected from O and S; and
R represents aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof. The present subject matter also relates to a method of making a dihydropyrimidinone derivative, a method of treating a gastrointestinal disease, a method of treating an ulcer, a pharmaceutical composition, and a method of making a pharmaceutical composition.

18 Claims, 9 Drawing Sheets

DIHYDROPYRIMIDINONE DERIVATIVES

BACKGROUND OF THE INVENTION

1. Field of the Invention

The present subject matter relates to dihydropyrimidinone derivatives, and particularly to 4-(substituted phenyl)-5-[4-(piperidin-1-yl) benzoyl]-3, 4-dihydropyrimidin-2(1H)-one derivatives.

2. Description of the Related Art

Peptic Ulcer Disease (PUD) is a gastrointestinal disease prevalent in a large population of the world. Complex gastric mucosal damage associated with PUD occurs from an imbalance between the gastro protective factors e.g., (prostaglandin, mucin, bicarbonate, blood supply, nitric oxide, etc.) and the aggressive factors (pepsin, gastric acid, etc.) present in the gastric mucosa. Risk factors of getting PUD include Helicobacter pylori infection, frequent use of non-steroidal anti-inflammatory drugs, and stress-induced mucosal damage.

Many anti-ulcer drugs mainly focus on decreasing the gastric acid secretion and/or increasing the mucosal defense system. Examples of anti-secretory drugs include Ranitidine (and other histamine H2 receptor antagonists), Omeprazole (and other irreversible proton pump inhibitors), and antacids. These drugs treat PUD by reducing or neutralizing the gastric acid, but have serious side effects when used for long times, such as hypergastrinemia, osteoporosis, development a carcinoids, and increased risk of bacterial infection.

Sucralfate may also be used for the treatment of gastric ulceration. However, sucralfate does not exhibit positive results for ulceration caused by non-steroid anti-inflammatory drugs (NSAIDs). Ulcers associated with NSAIDs may be prevented by Misoprostol (analogue of prostaglandin E1), which has a limited application due to abnormal side effects. Therefore, a need for potent anti-ulcer agents with improved safety profiles exists.

Pyrimidines have played an important role in medicinal chemistry and are important in the field of medicinal chemistry because of their potential biological activities, such as anti-tumor, anti-virus, and anti-bacterial activities. Some pyrimidines have been used as potential anti-hypertensive agents. 4-Aryl-1,4-dihydropyridines, like Nifedipine, was first introduced into clinical medicine in 1975 as an anti-hypertensive.

Moreover, dihydropyridines are the most potent calcium channel modulators available for the treatment of various cardiovascular diseases. Anti-ulcer activities have been reported for several calcium channel blockers, including Nifedipine.

Compounds containing dihydropyrimidinone and piperidine may have significant potential for the treatment of ulcers, according to a literature study. Dihydropyrimidines, also known as Biginelli compounds, are associated with a broad spectrum of biological activities, and some derivatives of dihydropyrimidine have been reported to possess potent anti-ulcer and anti-secretory activity.

Thus, providing a dihydropyrimidinone derivative as an anti-ulcer agent to solve the aforementioned problems is desired.

SUMMARY OF THE INVENTION

Dihydropyrimidinone derivatives include 4-(substituted phenyl)-5-[4-(piperidin-1-yl) benzoyl]-3, 4-dihydropyrimidin-2(1H)-one derivatives having a chemical structure according to Formula 1:

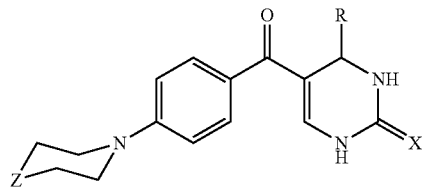

(Formula 1)

wherein
Z is selected from $CH_2$, O, and N;
X is selected from O and S; and
R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

An embodiment of the present subject matter is directed to a method of treating a gastrointestinal disease, including administering to a patient in need thereof at least one dihydropyrimidinone derivative.

An embodiment of the present subject matter is directed to a pharmaceutical composition including non-toxic, inert pharmaceutical suitable excipients, and one or more active compounds including at least one dihydropyrimidinone derivative of the present subject matter.

An embodiment of the present subject matter is directed to a method of making a pharmaceutical composition according to the present subject matter including mixing the dihydropyrimidirione derivative under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of treating an ulcer, including administering to a patient in need thereof a therapeutically effective amount of a pharmaceutical composition according to the present subject matter.

An embodiment of the present subject matter is directed to a method of making a dihydropyrimidinone derivative, including refluxing 1-[4-(piperidin-1-yl) phenyl] ethan-1-one (0.01 mol) with dimethylforamide dimethylacetal (DMF-DMA) (0.013 mol) to obtain enaminone; and refluxing a solution of enaminone (0.01 mol), substituted benzaldehyde (0.01 mol), and urea (0.01 mol) to yield dihydropyrimidinone derivatives having a structure of:

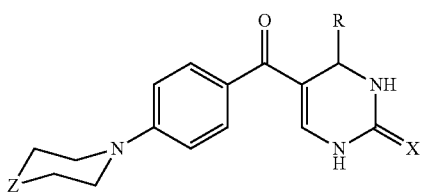

wherein
Z is selected from $CH_2$, O, and N;
X is selected from O and S; and
R represents an aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
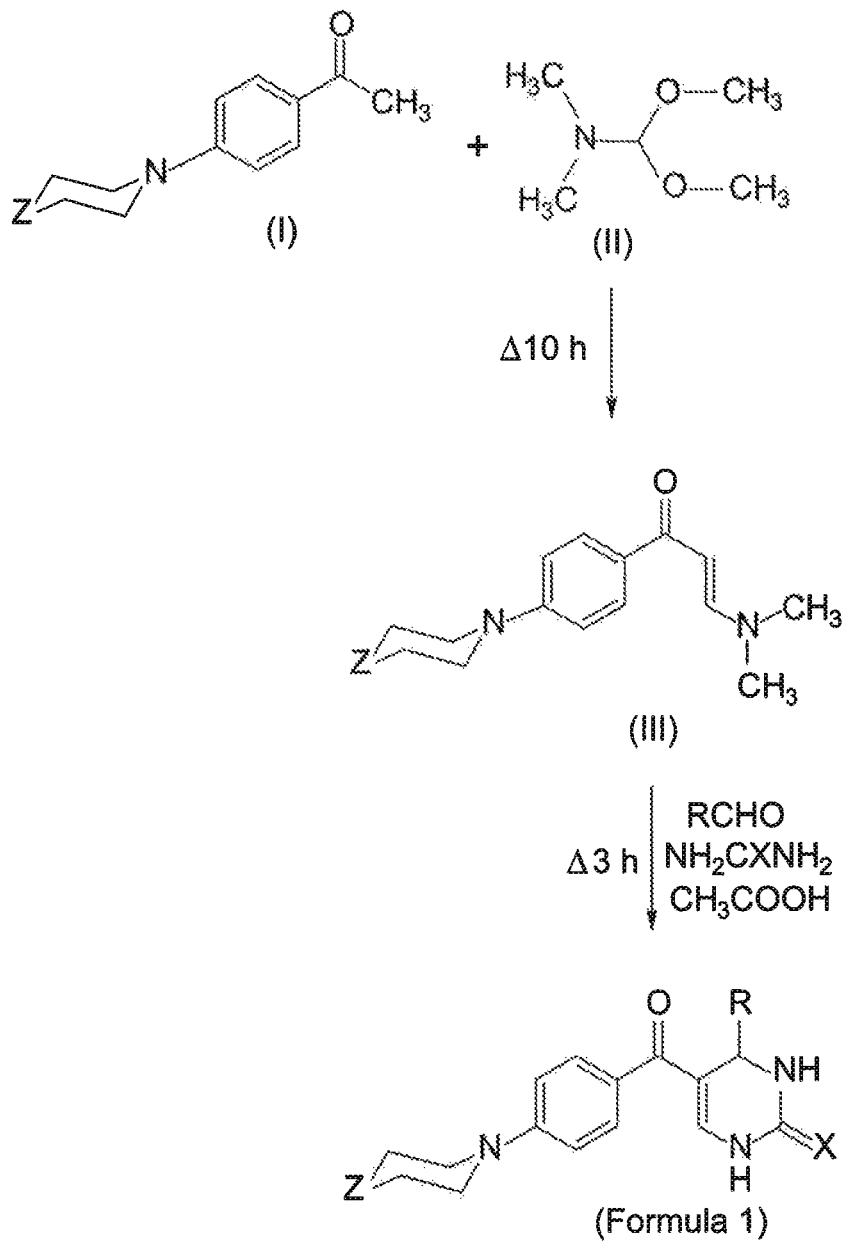
FIG. 1 illustrates the reaction scheme by which the dihydropyrimidinone derivatives can be prepared.

A dihydropyrimidinone derivative includes a compound having a chemical structure according to Formula 1, shown below.

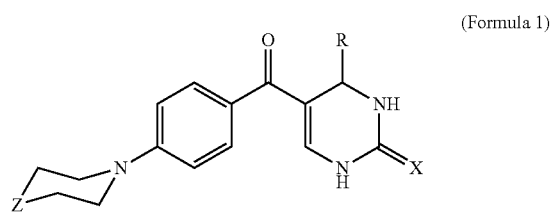

(Formula 1)

wherein

Z is selected from $CH_2$, O, and N;

X is selected from O and S; and

R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

In an embodiment, R represents mono- or di-substituted phenyl compounds. In an embodiment, R is selected from 2-nitro phenyl, 3-nitro phenyl, 4-nitro phenyl, 4-chloro phenyl, 2,4-dichloro phenyl, 3,4-dimethoxy phenyl, 2-methoxy phenyl, 4-hydroxy phenyl, 3-hydroxy phenyl, dimethylamino phenyl, 3-methoxy phenyl, 4-ethoxy phenyl, 2,4,5-trimethoxy phenyl, 2,3,4-trimethoxy phenyl, 3,4,5-trimethoxy phenyl, 2,4,6-trimethoxy phenyl, and 2,4-dimethoxy phenyl.

The dihydropyrimidinone derivatives can include 4-(substituted phenyl)-5-[4-(piperidin-1-yl) benzoyl]-3, 4-dihydropyrimidin-2(1H)-one derivatives. In an embodiment of the present subject matter, the dihydropyrimidinone derivatives include compounds N1-N-18 provided below:

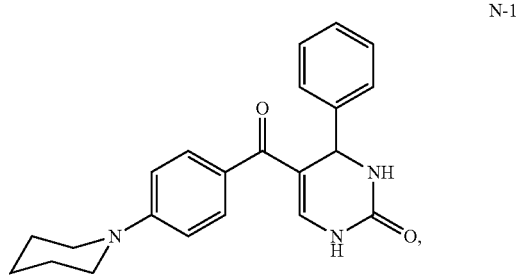

N-1

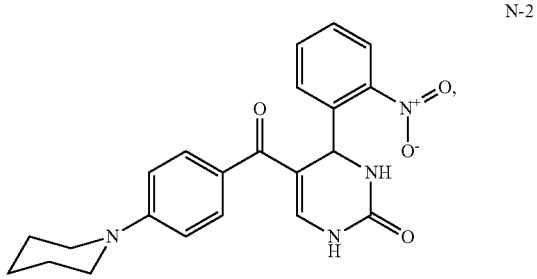

N-2

N-3
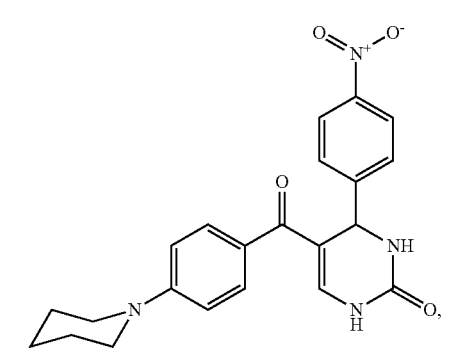
N-4
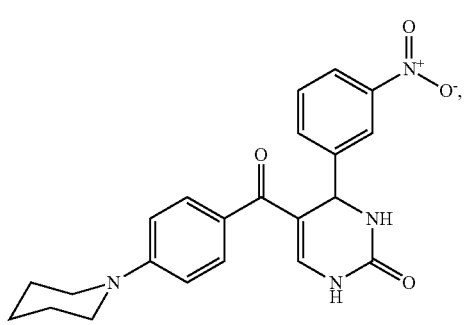
N-5
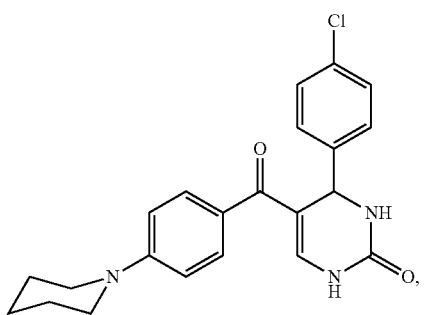
N-6
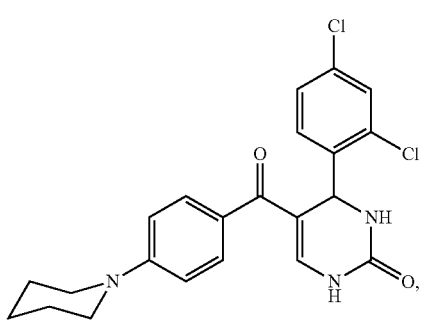
N-7
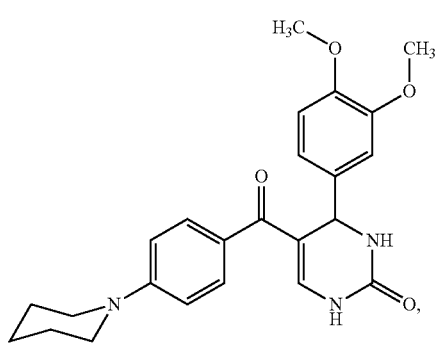
N-8
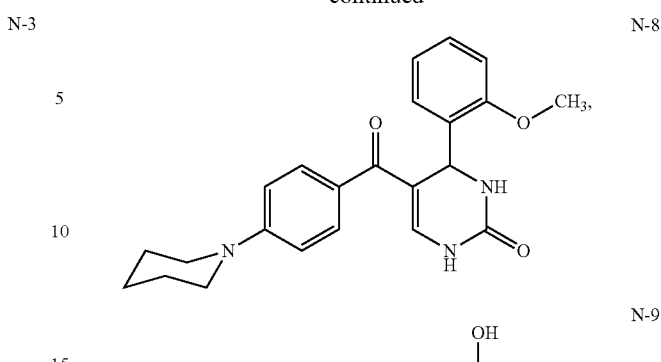
N-9
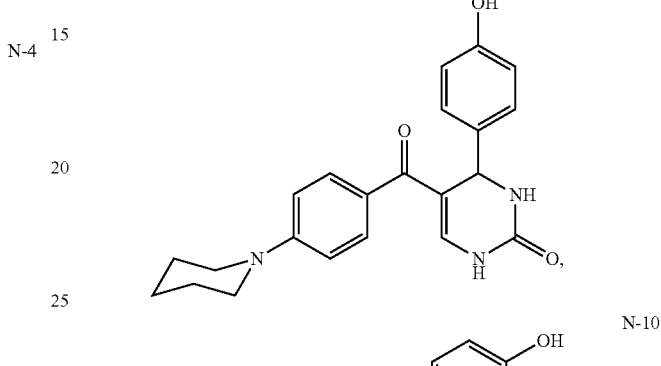
N-10
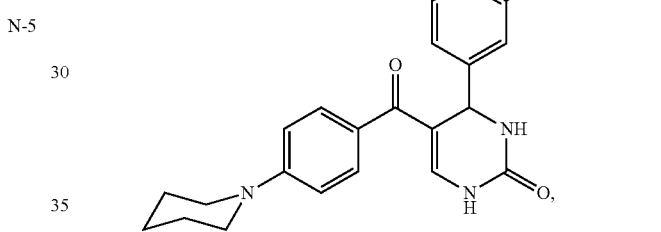
N-11
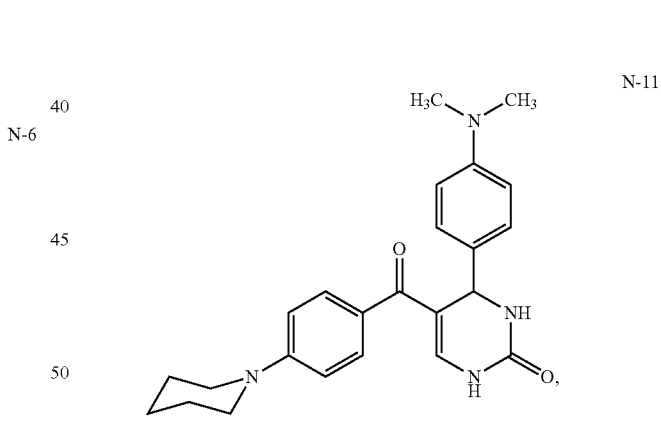
N-12
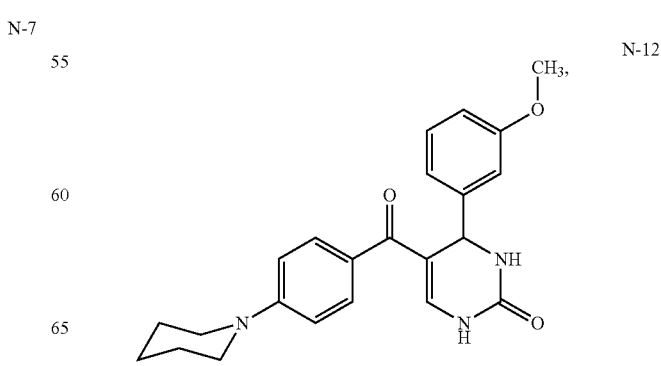

N-13
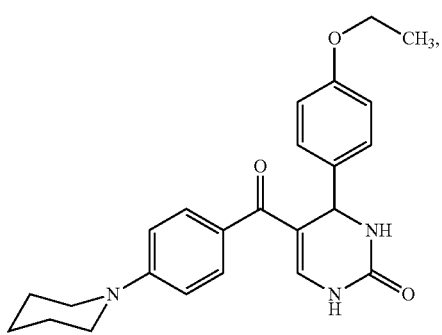

N-14
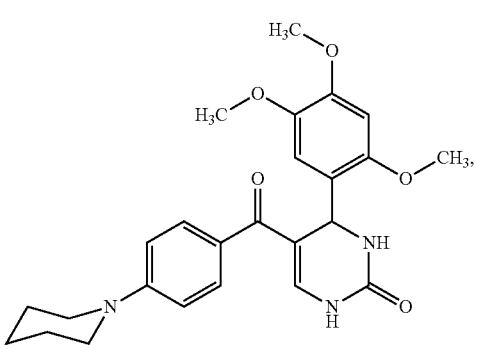

N-15
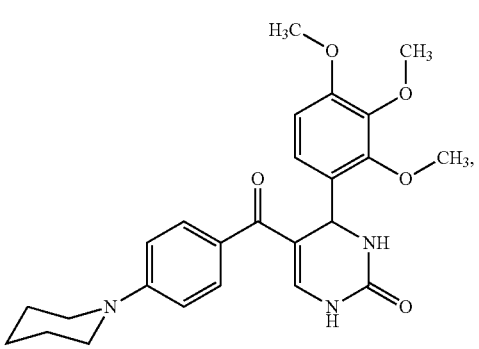

N-16
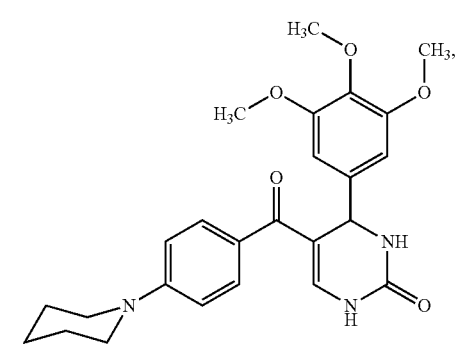

N-17
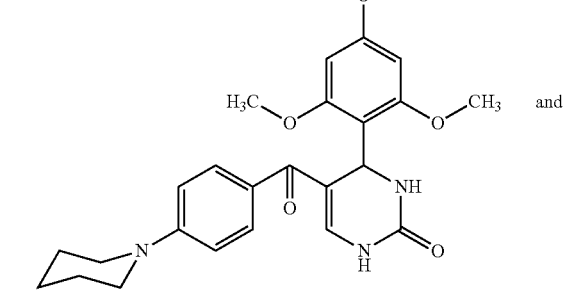

and

N-18
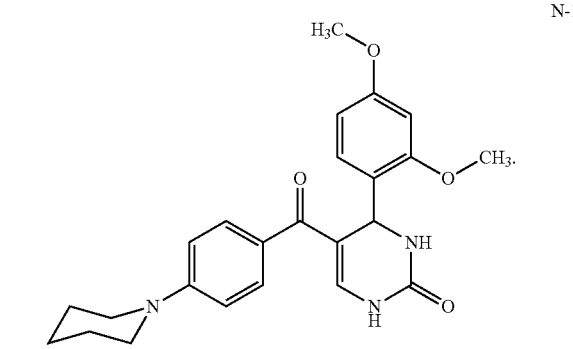

In an embodiment, the dihydropyrimidinone derivative is an anti-ulcer agent.

According to an embodiment, a method of treating diseases susceptible to treatment with an anti-ulcer agent can include administering to a patient in need thereof at least one of the dihydropyrimidinone derivative compounds disclosed herein.

In an embodiment, the diseases susceptible to treatment with an anti-ulcer agent can include diseases known to be associated with hyper secretion of gastric acid. For example, the diseases susceptible to treatment with the anti-ulcer agent can include at least one of gastric ulcers, gastroesophagal reflux, and Zollinger-Elisson syndrome.

An embodiment of the present subject matter is directed to a pharmaceutical composition comprising non-toxic, inert pharmaceutically suitable excipients, and one or more active compounds comprising at least one of the dihydropyrimidinone derivative compounds.

In an embodiment, the pharmaceutical composition of the present subject matter is in a form suitable for daily, weekly, or monthly administration.

In an embodiment, the form of the pharmaceutical composition is a tablet, pill, capsule, granule, powder, ointment, sterile parenteral solution or suspension, metered aerosol or liquid spray, drops, ampule, injection, teaspoonful, or suppository.

An embodiment of the present subject matter is directed to a method of making a pharmaceutical composition including mixing the dihydropyrimidinone derivative with a pharmaceutically acceptable carrier. For example, the method of making a pharmaceutical composition can include mixing the dihydropyrimidinone derivative under sterile conditions with a pharmaceutically acceptable carrier and preservatives, buffers, or propellants to create the pharmaceutical composition; and presenting the pharmaceutical composition in a form suitable for daily, weekly, or monthly administration.

An embodiment of the present subject matter is directed to a method of treating an ulcer, comprising administering to a patient in need thereof a therapeutically effective amount of a pharmaceutical composition according to the present subject matter.

In an embodiment, the composition of the present subject matter may be administered orally, nasally, rectally, parenterally, intracisternally, intra vaginally, intraperitoneally, topically, transdermally, or by surgical implantation. In an embodiment, the composition of the present subject matter is administered in a form selected from liquid oral preparations, solid oral preparations, parenteral preparations, injectable suspensions, and liposomes.

FIG. 1 depicts a reaction scheme by which the dihydropyrimidinone derivatives of Formula I can be prepared. As shown in FIG. 1, the dihydropyrimidinone derivatives can be synthesized by refluxing 1-[4-(piperidin-1-yl) phenyl] ethan-1-one I with dimethylforamide dimethylacetal (DMF-DMA) II to obtain enaminone III; and refluxing a solution of enaminone III, substituted benzaldehyde, urea, and Glacial acetic acid to yield the dihydropyrimidinone derivatives of Formula I, where Z, X, and R represent the molecules disclosed above.

In an embodiment, the 1-[4-(piperidin-1-yl) phenyl] ethan-1-one is refluxed with the dimethylforamide dimethylacetal (DMF-DMA) under a solvent free condition for about 10 hours.

In an embodiment, the solution of enaminone, substituted benzaldehyde, urea, and Glacial acetic acid is refluxed for about 3 hours.

In an embodiment, the method of making an anti-ulcer agent further includes recrystallizing the 4-(substituted phenyl)-5-[4-(piperidin-1-yl) benzoyl]-3,4-dihydropyrimidin-2 (1H)-one derivatives from the ethanol and Glacial acetic acid mixture.

The dihydropyrimidinone derivatives can be administered to a patient in need thereof. For example, the dihydropyrimidinone derivatives can be used to treat a patient suffering from a gastrointestinal disease. The gastrointestinal disease can include gastric ulcer, gastroesophagal reflux, Zollinger-Elisson syndrome, and/or other diseases associated with hyper secretion of gastric acid. Therefore, compounds according to Formula 1 may be used as anti-ulcer agents. The present subject matter is also directed to pharmaceutical formulations of the compounds according to Formula 1 in dosage units.

The dihydropyrimidinone derivatives or pharmaceutical compositions can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

An embodiment of the present subject matter is directed to a pharmaceutical composition including one or more of the dihydropyrimidinone derivatives. To prepare the pharmaceutical composition, one or more of the dihydropyrimidinone derivatives or a salt thereof, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

For parenteral use, the carrier will usually comprise sterile water, though other ingredients, for example, for purposes such as aiding solubility or for preservation, may be included. Injectable suspensions may also be prepared, in which case appropriate liquid carriers, suspending agents, and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The dihydropyrimidinone derivatives of the present disclosure also can be administered in the form of liposomes. Liposomes generally are derived from phospholipids or other lipid substances and are formed by mono- or multi-lamellar hydrated liquid crystals dispersed in an aqueous medium. Any nontoxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

The present compositions can include adjuvants such as preservatives, wetting agents, emulsifying agents, and dispersing agents. Prevention of the action of microorganisms can be ensured by the inclusion of various anti-bacterial and anti-fungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the dihydropyrimidinone derivative or an amount effective to treat a gastrointestinal disease, such as a disease associated with hyper secretion of gastric acid, may be determined initially from the Examples described herein and adjusted for specific desired dihydropyrimidinone derivatives using routine methods.

The following examples illustrate the present teachings.

EXAMPLE 1

Synthesis of the Dihydropyrimidinone Derivatives

As shown in FIG. 1, enaminone (III), (2E)-3-(dimethyl-amino)-1-[4-(piperidin-1-yl) phenyl] prop-2-en-1-one was synthesized by refluxing 1-[4-(piperidin-1-yl) phenyl] ethan-1-one (I) with dimethylforamide dimethylacetal (DMF-DMA) (II) under solvent free conditions for 10 hours.

The structure of the isolated product was confirmed by elemental analysis and spectral data. $^1$H NMR spectrum displayed two singles at δ 2.89, 3.17 ppm due to the N, N-dimethyl protons and two doublets at δ 5.77 and 7.65 ppm (J=12 Hz) due to the ethylenic protons, in addition to the multiplet at the region δ 6.89-7.78 ppm (4H, aromatic). The value of coupling constant (J=12.5 Hz) for the ethylenic protons indicated, that the enaminone (III) exist in the E-configuration. A single crystal X-ray structure also confirmed the three dimensional structure of enaminone (III). Cambridge Crystallographic Data Center (CCDC) number 1532826 contains crystallographic data for the structure (III).

Figure 2:
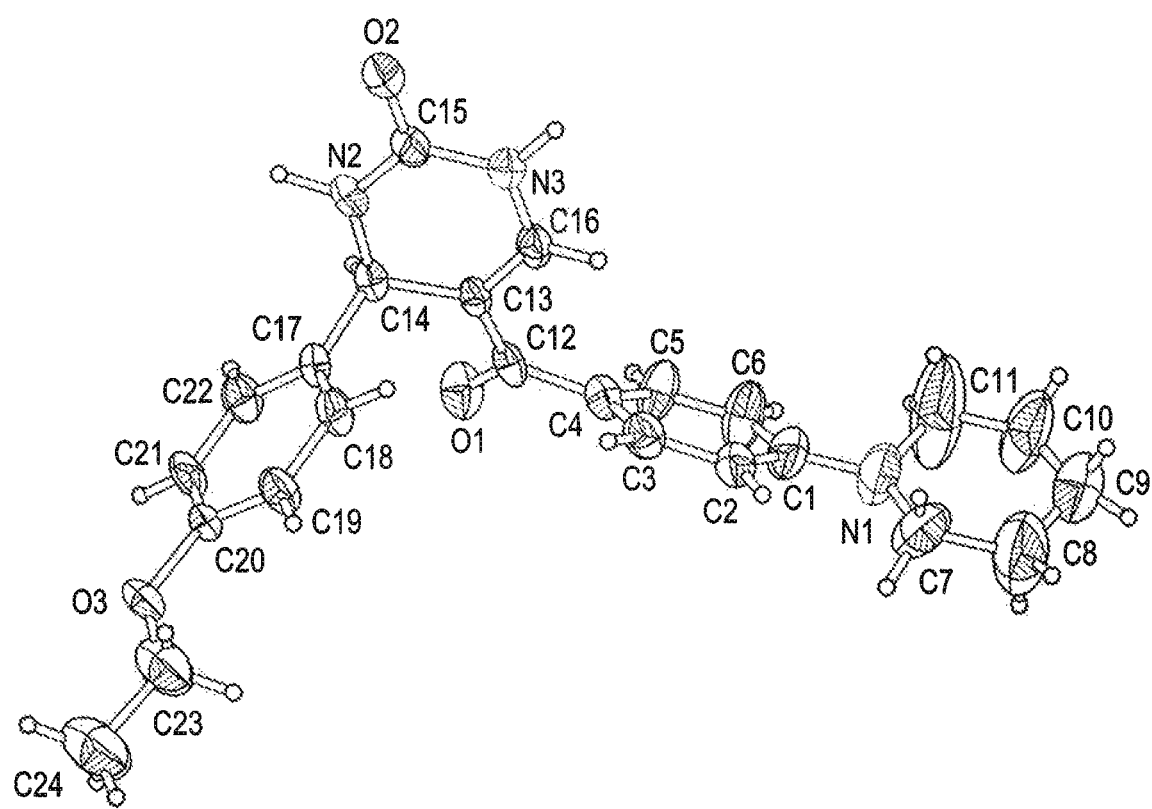
FIG. 2 illustrates the single crystal X-ray structure of dihydropyrimidinone derivative (N-13).
Figure 3:
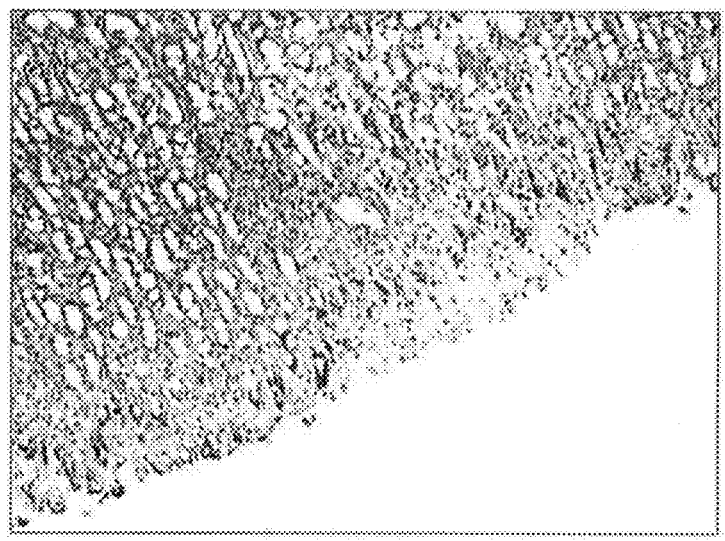
FIG. 3 is a microscopic image of an ethanol-induced gastric ulceration, shown with periodic acid Schiff (PAS) staining for sample treated with ethanol.
Figure 4:
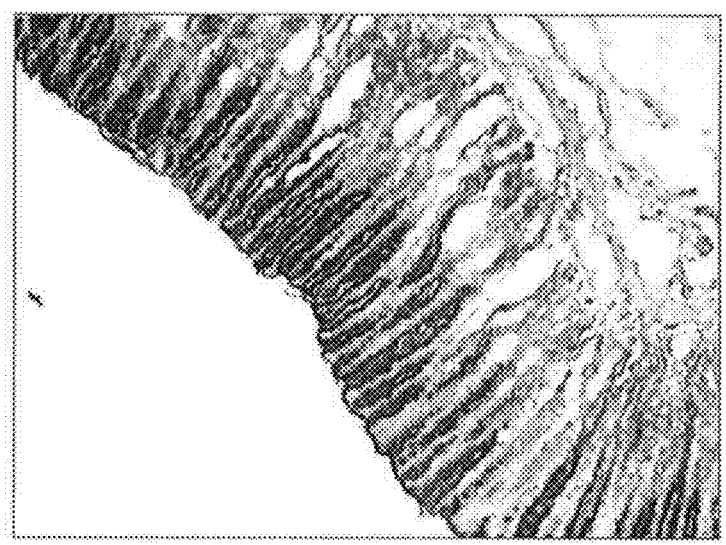
FIG. 4 is a microscopic image of an ethanol-induced gastric ulceration, shown with PAS staining for sample treated with standard drug Ranitidine (50 mg/kg).
Figure 5:
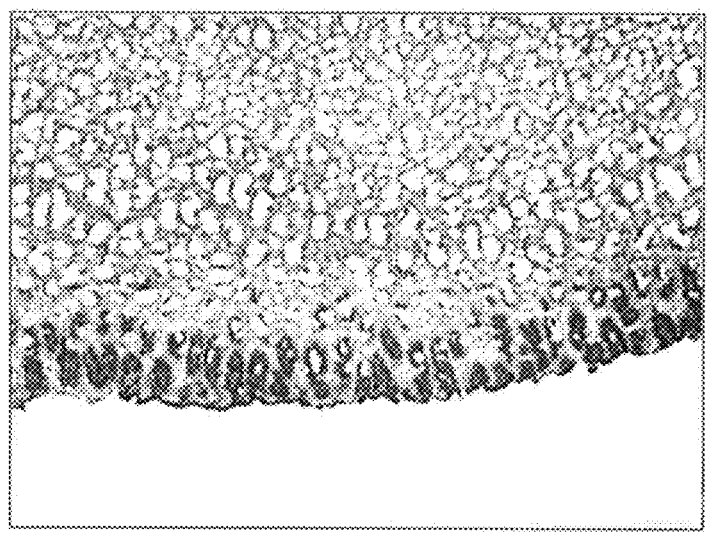
FIG. 5 is a microscopic image of an ethanol-induced gastric ulceration, shown with PAS staining for sample treated with anti-ulcer agent, N-3 (50 mg/kg) according to the present subject matter.
Figure 6:
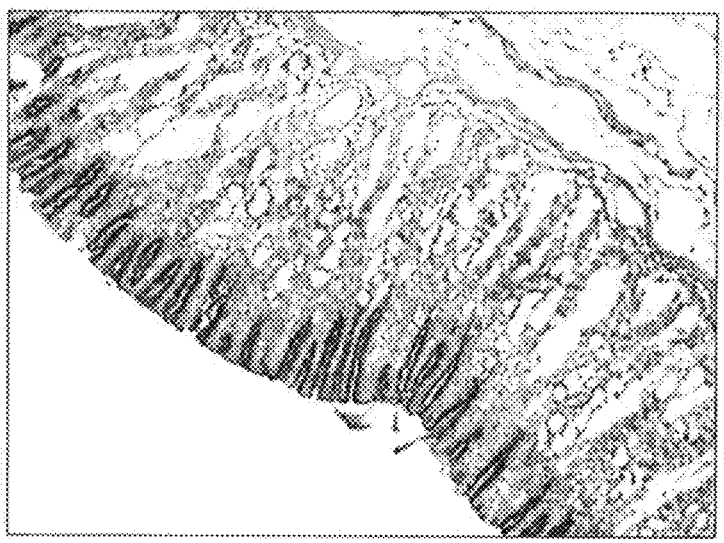
FIG. 6 is a microscopic image of an ethanol-induced gastric ulceration, shown with PAS staining for sample treated with anti-ulcer agent, N-8 (50 mg/kg) according to the present subject matter.
Figure 7:
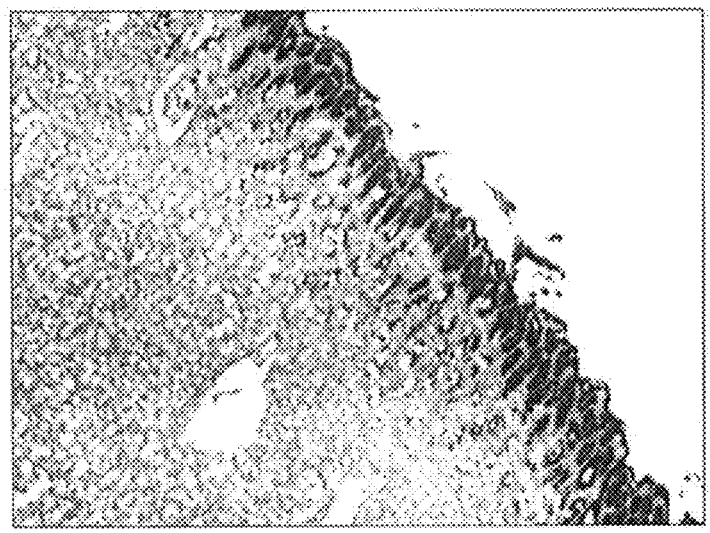
FIG. 7 is a microscopic image of an ethanol-induced gastric ulceration, shown with PAS staining for sample treated with anti-ulcer agent, N-11 (50 mg/kg) according to the present subject matter.
Figure 8:
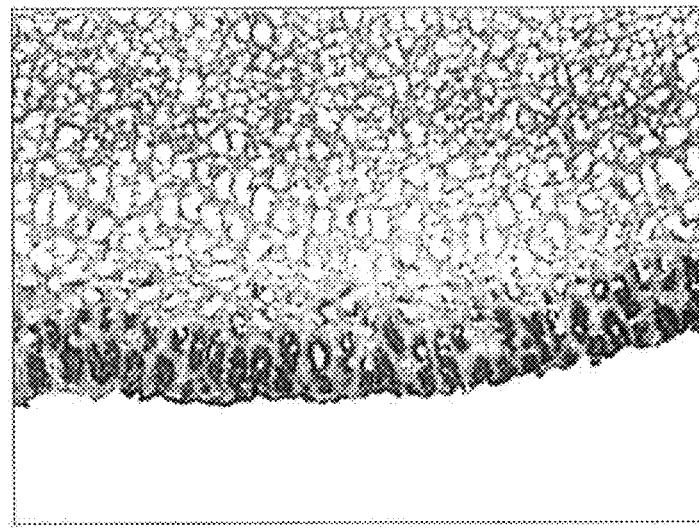
FIG. 8 is a microscopic image of an ethanol-induced gastric ulceration, shown with PAS staining for sample treated with anti-ulcer agent, N-15 (50 mg/kg) according to the present subject matter.
Figure 9:
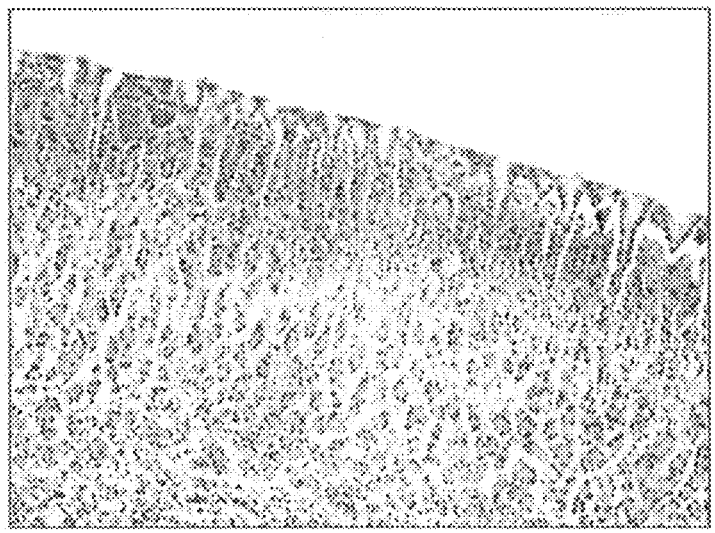
FIG. 9 is a microscopic image of as gastric section taken from the rat treated with 80% ethanol.
Figure 10:
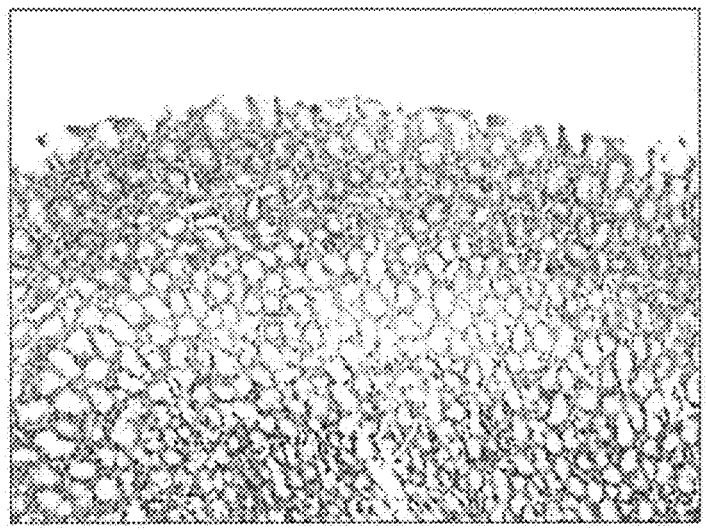
FIG. 10 is a microscopic image of as gastric section taken from the rat treated with standard drug Ranitidine (50 mg/kg).
Figure 11:
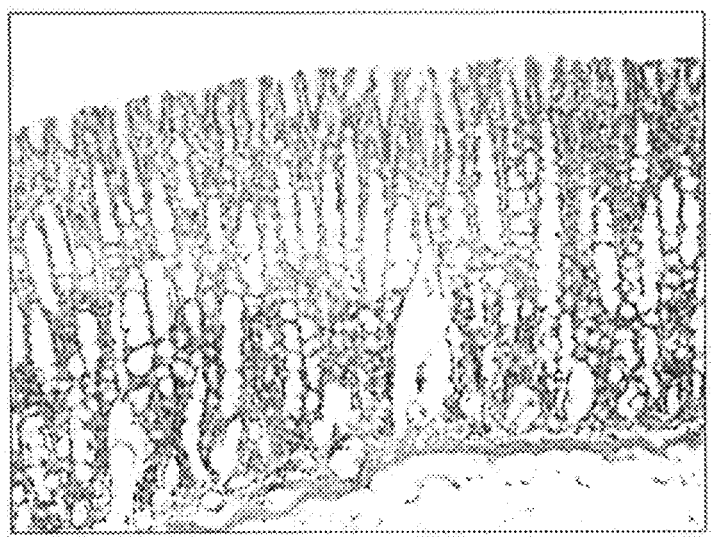
FIG. 11 is a microscopic image of as gastric section taken from gastric specimen of rat treated with N-3 (50 mg/kg).
Figure 12:
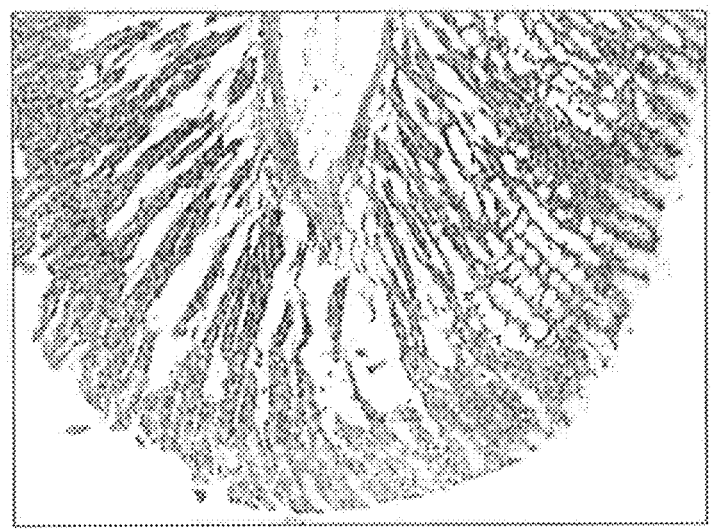
FIG. 12 is a microscopic image of as gastric section taken from gastric specimen of rat treated with N-8 (50 mg/kg).
Figure 13:
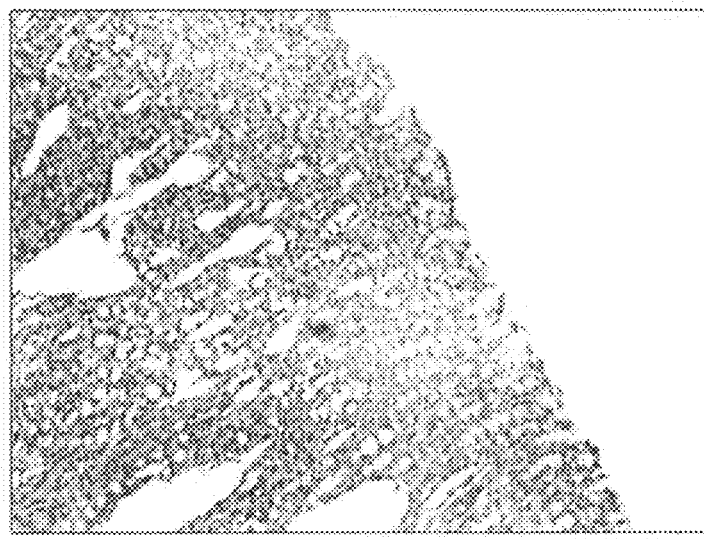
FIG. 13 is a microscopic image of as gastric section taken from gastric specimen of rat treated with N-11 (50 mg/kg).
Figure 14:
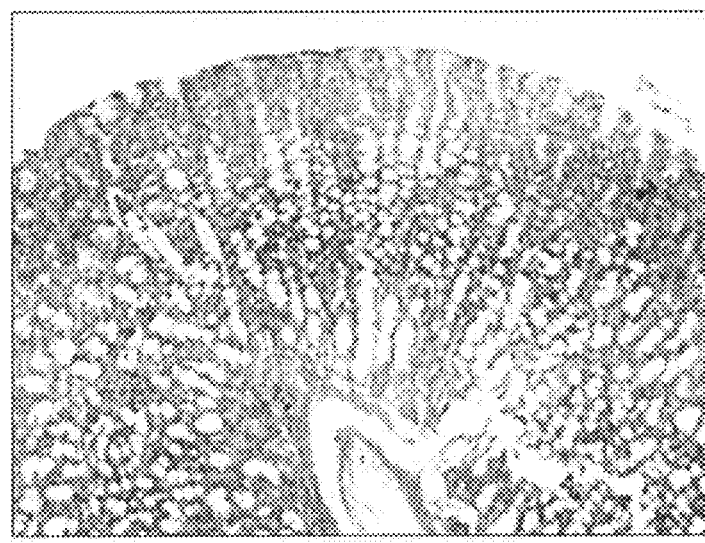
FIG. 14 is a microscopic image of as gastric section taken from gastric specimen of rat treated with N-15 (50 mg/kg).

To prepare the final dihydropyrimidinone derivatives, a solution of enaminone (III) (0.01 mol), substituted benzaldehyde (0.01 mol), urea (0.01 mol), and Glacial acetic acid (10 mL) was heated under reflux for 3 hours. The precipitates (Compounds N-1 to N-18) thus formed were collected by filtration, washed with water and recrystallized from Glacial acetic acid and ethanol mixture. In the $^1$H-NMR spectra, the signals of the individual protons of the compounds were verified on the basis of multiplicity, chemical shifts and the coupling constant. All of the compounds showed the $D_2O$ exchangeable broad singlet at δ 6.97-7.31 ppm and δ 9.07-9.67 ppm corresponding to the two NH protons. Analytical and spectral data for the compounds were in good agreement with the expected structures of the compounds. The single crystal X-ray structure confirms the three dimensional structure of dihydropyrimidinone derivative N-13 (FIG. 2). Cambridge Crystallographic Data Center (CCDC) number 1532825 contains crystallographic data for the structure N-13.

The spectral data for compounds N-1 to N-18 are provided below.

Compound N-1 4-Phenyl-5-[4-(piperidin-1-yl) benzoyl]-3, 4-dihydropyrimidin-2(1H)-one (N-1): Color: yellow; Yield: 50%; M.p.: 220-222° C.; UV λmax (Methanol)=404 nm; IR (KBr) cm$^{-1}$: 3273 (N—H), 2800 (ArC—H), 1675 (C═O), 1636 (C═O), 1618 (C═C); 1H NMR (500 MHz, DMSO-d6): δ=1.56 (8H, s, 4×—CH2, piperidine), 2.74 (1H, s, —CH, piperidine), 2.89 (1H, s, —CH, piperidine), 5.46 (1H, s, H-4), 6.9 (2H, d, J=8.5 Hz, Ar—H), 7.0 (1H, s, NH, $D_2O$ exchg.), 7.25-7.43 (7H, m, Ar—H), 7.78 (1H, s, ═CH), 9.18 (1H, s, —CONH, $D_2O$ exchg.); 13C NMR (125.76 MHz, DMSO-d6): δ=24.4, 25.3, 31.2, 36.2, 48.0, 48.5, 48.6, 54.1, 113.0, 113.8, 126.8, 127.2, 127.7, 128.9, 130.7, 139.3, 144.7, 152.0, 153.6, 162.7, 190.5; MS: m/z=360.79 [M]+; Analysis for $C_{22}H_{23}N_3O_2$: C (73.11) H (6.41) N (11.63)%; found C (73.39) H (6.43) N (11.60)%.

Compound N-2 4-(2-Nitrophenyl)-5-[4-(piperidin-1-yl) benzoyl]-3,4-dihydropyrimidine-2(1H)-one (N-2): Color: brown; Yield: 60%; M.p.: 190-192° C.; UV λmax (Methanol)=426 nm; IR (KBr) cm$^{-1}$: 3443 (N—H), 2852 (ArC—H), 1634 (C═O), 1595 (C═O), 1567 (C═C); 1H NMR (500 MHz, DMSO-d6): δ=δ=1.54 (8H, s, 4×—CH2, piperidine), 3.44 (1H, s, —CH, piperidine), 3.48 (1H, s, —CH, piperidine), 6.11 (1H, s, H-4), 6.89 (2H, d, J=9.0 Hz, Ar—H), 7.14 (1H, s, NH, $D_2O$ exchg.), 7.38-7.89 (8H, m, Ar—H), 8.10 (1H, s, ═CH), 9.42 (1H, s, —CONH, $D_2O$ exchg.); 13C NMR (125.76 MHz, DMSO-d6): δ=19.0, 24.4, 25.3, 48.5, 50.1, 56.5, 1117.7, 123.8, 124.4, 126.7, 129.1, 130.0, 130.7, 134.3, 138.8, 140.3, 148.3, 151.2, 153.6, 190.1; MS: m/z=403.80 [M-2]+; Analysis for $C_{22}H_{22}N_4O_4$: C (65.01) H (5.46) N (13.78)%; found C (65.26) H (5.47) N (13.73)%.

Compound N-3 4-(4-Nitrophenyl)-5-[4-(piperidin-1-yl) benzoyl]-3,4-dihydropyrimidin-2(1H)-one (N-3): Color: yellow; Yield: M.p.: 180-182° C.; UV λmax (Methanol)=405 nm; IR (KBr) cm$^{-1}$: 3273 (N—H), 2800 (ArC—H), 1675 (C═O), 1636 (C═O), 1618 (C═C); 1H NMR (500 MHz, DMSO-d6): δ=1.55 (8H, s, 4×—CH2, piperidine), 2.73 (1H, s, —CH, piperidine), 2.89 (1H, s, —CH, piperidine), 5.58 (1H, s, H-4), 6.89 (2H, d, J=9.0 Hz, Ar—H), 7.09 (1H, s, NH, $D_2O$ exchg.), 7.41-7.93 (8H, m, Ar—H), 8.21 (1H, s, ═CH), 9.35 (1H, s, —CONH, $D_2O$ exchg.); 13C NMR (125.76 MHz, DMSO-d6): δ=19.0, 24.4, 25.3, 48.5, 54.0, 56.5, 111.9, 113.8, 124.2, 126.9, 128.2, 130.7, 140.1, 147.1, 151.7, 151.8, 153.6, 190.2; MS: m/z=406.00 [M]+; Analysis for $C_{22}H_{22}N_4O_4$ : C (65.01) H (5.46) N (13.78)%; found C (65.25) H (5.46) N (13.72)%.

Compound N-4 4-(3-Nitrophenyl)-5-[4-(piperidin-1-yl) benzoyl]-3,4-dihydropyrimidin-2(1H)-one (N-4): Color: yellow; Yield: M.p.: 185-187° C.; UV λmax (Methanol)= 404 nm; IR (KBr) cm$^{-1}$: 3256 (N—H), 2800 (ArC—H), 1701 (C═O), 1685 (C═O), 1654 (C═C); 1H NMR (500

MHz, DMSO-d6): δ=1.55 (8H, s, 4×—CH$_2$, piperidine), 2.73 (1H, s, —CH, piperidine), 2.89 (1H, s, —CH, piperidine), 5.58 (1H, s, H-4), 6.89 (2H, d, J=9.0 Hz, Ar—H), 7.09 (1H, s, NH, D2O exchg.), 7.41-7.93 (8H, m, Ar—H), 8.21 (1H, s, =CH), 9.35 (1H, s, —CONH, D2O exchg.); 13C NMR (125.76 MHz, DMSO-d6): δ=19.0, 24.4, 25.3, 48.5, 54.0, 56.5, 111.9, 113.8, 124.2, 126.9, 128.2, 130.7, 140.1, 147.1, 151.7, 151.8, 153.6, 190.2; MS: m/z=406.21 [M]+; Analysis for C$_{22}$H$_{22}$N$_4$O$_4$ : C (65.01) H (5.46) N (13.78)%; found C (65.24) H (5.45) N (13.71)%.

Compound N-5 4-(4-Chlorophenyl)-5-[4-(piperidin-1-yl) benzoyl]-3,4-dihydropyrimidin-2(1H)-one (N-5); Color: yellow; Yield: 70%; M.p.: 230-232° C.; UV λmax (Methanol)=421 nm; IR (KBr) cm$^{-1}$: 3261 (N—H), 2931 (ArC—H), 1654 (C=O), 1636 (C=O), 1600 (C=C); 1H NMR (500 MHz, DMSO-d6): δ=57 (8H, s, 4×—CH$_2$, piperidine), 2.73 (1H, s, —CH, piperidine), 2.89 (1H, s, piperidine), 5.44 (1H, s, H-4), 6.9 (2H, d, J =7.0 Hz, Ar—H), 7.0 (1H, s, NH, D$_2$O exchg.), 7.33-7.40 (6H, m, Ar—H), 7.81 (1H, s, =CH), 9.34 (1H, s, —CONH, D$_2$O exchg.); 13C NMR (125.76 MHz, DMSO-d6): δ=24.4, 25.3, 31.2, 36.2, 48.5, 53.6, 112.5, 113.8, 127.1, 128.7, 128.8, 130.7, 132.3, 139.6, 143.7, 151.9, 153.6, 190.4.; MS: m/z=395.82 [M]+; Analysis for C$_{22}$H$_{22}$ClN$_3$O$_2$: C (66.75) H (5.60) N (10.61)%; found C (66.50) H (5.61) N (10.62)%.

Compound N-6 4-(2,4-Dichlorophenyl)-5-[4-(piperidin-1-yl) benzoyl]-3,4-dihydropyrimidin-2(1H)-one (N-6): Color: yellow; Yield: 75%; M.p.: 195-197° C.; UV λmax (Methanol)=406 nm; IR (KBr) cm-1: 3273 (N—H), 2800 (ArC—H), 1671 (C=O), 1630 (C—O), 1615 (C=C); 1H NMR (500 MHz, DMSO-d6): δ=1.55 (8H, s, 4×—CH$_2$, piperidine), 3.2 (2H, s, —CH, piperidine), 5.83 (1H, s, H-4), 6.89 (2H, d, J=8.5 Hz, Ar—H), 7.10 (1H, s, NH, D$_2$O exchg.), 7.39-7.56 (7H, m, Ar—H), 7.75 (1H, s, =CH), 9.32 (1H, s, —CONH, D$_2$O exchg.); 13C NMR (125.76 MHz, DMSO-d6): δ=19.0, 24.4, 25.3, 48.5, 52.4, 56.5, 111.0, 113.8, 127.6, 128.1, 129.4, 130.76, 131.36, 133.1, 133.5, 140.3, 151.2, 153.6, 190.1 MS: m/z=430.54 [M]+; Analysis for C$_{22}$H$_{21}$Cl$_2$N$_3$O$_2$: C (61.40) H (4.92) N (9.76)%; found C (61.60) H (4.93) N (9.75)%.

Compound N-7 4-(3,4-Dimethoxyphenyl)-5-[4-(piperidin-1-yl)benzoyl]-3,4-dihydropyrimidin-2(1H)-one (N-7): Color: brown; Yield: 70%; M.p.: 145-147° C.; UV λmax (Methanol)=434 nm; IR (KBr) cm$^{-1}$: 3478 (N—H), 2788 (ArC—H), 1634 (C=O), 1596 (C=O), 1567 (C=C); 1H NMR (500 MHz, DMSO-d6): δ=1.56 (8H, s, 4×—CH$_2$, piperidine), 3.28 (2H, s, —CH, piperidine), 3.7 (6H, s, 2×—OCH$_3$), 5.42 (1H, s, H-4), 6.83-6.84 (4H, m, Ar—H), 7.0 (1H, s, NH, D$_2$O exchg.), 6.89-7.46 (8H, m, Ar—H), 7.73 (1H, s, =CH), 9.18 (1H, s, —CONH, D$_2$O exchg.); 13C NMR (125.76 MHz, DMSO-d6): δ=15.6, 19.0, 24.4, 25.3, 48.0, 49.0, 53.7, 55.9, 56.5, 63.3, 110.9, 112.1, 112.9, 113.9, 118.7, 127.3, 130.7, 148.5, 149.9, 152.0, 153.6, 190.6; MS: m/z=422.18 [M+1]+; Analysis for C$_{24}$H$_{27}$N$_3$O$_4$: C (68.39) H (6.46) N (9.97)%; found C (68.57) H (6.47) N (9.99)%.

Compound N-8 4-(2-Methoxyphenyl)-5-[4-(piperidin-1-yl) benzoyl]-3,4-dihydropyrimidin-2(1H)-one (N-8): Color: yellow; Yield: 50%; M.p.: 160-162° C.; UV λmax (Methanol)=429 nm; IR (KBr) cm$^{-1}$: 3441 (N—H), 2931 (ArC—H), 1634 (C=O), 1595 (C=O), 1530 (C=C); 1H NMR (500 MHz, DMSO-d6): δ=1.57 (8H, s, 4×—CH$_2$, piperidine), 2.73 (1H, s, —CH, piperidine), 2.87 s, piperidine), 3.81 (3H, s, —OCH$_3$), 5.73 (1H, s, H-4), 6.87-7.25 (8H, m, Ar—H), 7.31 (1H, s, NH, D$_2$O exchg.), 7.45 (1H, s, =CH), 9.13 (1H, s, —CONH, D$_2$O exchg.); 13C NMR (125.76 MHz, DMSO-d6): δ=24.4, 25.3, 48.5, 49.6, 55.9, 112.9, 130.7, 152.2, 153.3, 190.1; MS: m/z=391.00 [M]+; Analysis C$_{23}$H$_{25}$N$_3$O$_3$:C (70.57) H (6.44) N (10.73)%; found C (70.82) H (6.43) N (10.75)%.

Compound N-9 4-(4-Hydroxyphenyl)-5-[4-(piperidin-1-yl) benzoyl]-3,4-dihydropyrimidin-2(1H)-one (N-9): Color: brown; Yield: 45%; M.p.: 210-212° C.; UV λmax (Methanol)=404 nm; IR (KBr) cm$^{-1}$: 3270 (N—H), 2930 (ArC—H), 1670 (C=O), 1593 (C=O), 1508 (C=C); 1H NMR (500 MHz, DMSO-d6): δ=1.55 (8H, s, 4×—CH$_2$, piperidine), 2.73 (1H, s, —CH, piperidine), 2.88 (1H, s, —CH, piperidine), 5.37 (1H, s, H-4), 6.71-6.99 (8H, m, Ar—H), 7.14 (1H, s, NH, D$_2$O exchg.), 7.95 (1H, s, =CH), 9.20 (1H, s, —CONH, D$_2$O exchg.), 9.90 (1H, s, OH, D$_2$O exchg.); 13C NMR (125.76 MHz, DMSO-d6): δ=15.6, 24.4, 25.3, 31.2, 36.2, 48.0, 48.5, 53.6, 65.4, 113.4, 113.8, 115.5, 116.3, 127.3, 128.0, 130.7, 132.5, 135.3, 138.7, 152.1, 153.9, 157.1, 162.7, 190.6; MS: m/z=379.61 [M+2]+; Analysis for C22H23N3O3: C (70.01) H (6.14) N (11.13)%; found C (70.25) H (6.15) N (11.11)%.

Compound N10 4-(3-Hydroxyphenyl)-5-[4-(piperidin-1-yl) benzoyl]-3,4-dihydropyrimidin-2(1H)-one (N-11): Color: black; Yield: 45% M.p.: 190-192° C.; λmax (Methanol)=420 nm; IR, (KBr) cm$^{-1}$:3200 (N—H), 2930 (ArC—H), 1654 (C=O), 1636 (C=O), 1600 (C=C); 1H NMR (500 MHz, DMSO-d6): δ1.55 (8H, s, 4×—CH$_2$, piperidine), 2.73 (1H, s, —CH, piperidine), 2.87 (1H, s, —CH, piperidine), 5.40 (1H, s, H-4), 6.7-6.9 (8H, m, Ar—H), 7.0 (1H, s, NH, D$_2$O exchg.), 7.95 (1H, s, =CH), 9.30 (1H, s, —CONH, D$_2$O exchg.), 9.70 (1H, s, OH, D$_2$O exchg.); 13C NMR (125.76 MHz, DMSO-d6): δ=15.6, 21.6, 24.4, 25.3, 25.7, 31.1, 36.2, 48.0, 48.5, 53.9, 65.4, 113.2, 113.6, 113.8, 114.7, 117.3, 127.2, 129.8, 130.7, 138.9, 146.1, 152.2, 153.6, 157.9, 162.7, 172.7, 190.5; MS: m/z=376.94 [M]+; Analysis for C$_{22}$H$_{23}$N$_3$O$_3$:C (70.01) H (6.14) N (11.13)%; found C (70.24) H (6.14) N (11.10)%.

Compound N-11 4-(4-Dimethylamino phenyl)-5-[4-(piperidin-1-yl) benzoyl]-3,4-dihydropyrimidin-2(1H)-one (N-11): Color: black; Yield: 40%; M.p.: 185-187° C.; UV λmax (Methanol)=435; IR (KBr) cm-1: 3479 (N—H), 2788 (ArC—H), 1634 (C=O), 1596 (C=O), 1567 (C=C); 1H NMR (500 MHz, DMSO-d6): δ=1.56 (8H, s, 4×—CH$_2$, piperidine), 2.81 (2H, s, —CH, piperidine), 3.0 (6H, s, —N(CH$_3$)$_2$, 5.30 (1H, s, H-4), 6.7-6.9 (8H, m, Ar—H), 7.0 (1H, s, NH, D$_2$O exchg.), 7.69 (1H, s, =CH), 9.67 (1H, s, —CONH, D$_2$O exchg.); 13C NMR (125.76 MHz, DMSO-d6): δ=15.6, 24.4, 25.3, 48.0, 48.5, 65.3, 111.5, 113.2, 130.9, 131.9, 132.8, 154.6, 190.2; MS: m/z=405.20 [M+]+; Analysis for C$_{24}$H$_{28}$N$_4$O$_2$:C (71.26) H (6.98) N (13.85)%; found C (71.01) H (6.96) N (13.84)%.

Compound N-12 4-(3-Methoxyphenyl)-5-[4-(piperidin-1-yl) benzoyl]-3,4-dihydropyrimidin-2(1H)-one (N-12): Color: yellow; Yield: 50%; M.p.: 160-162° C.; UV λmax (Methanol)=432; IR (KBr) cm$^{-1}$: 3246 (N—H), 2929 (ArC—H), 1701 (C=O), 1654 (C=O), 1600 (C=C); 1H NMR (500 MHz, DMSO-d6): δ=1.57 (8H, s, 4×—CH2, piperidine), 2.7 (1H, s, —CH, piperidine), 2.80 (1H, s, —CH, piperidine), 3.72 (3H, s, —OCH$_3$), 5.43 (1H, s, H-4), 6.82-6.93 (6H, m, Ar—H), 7.0 (1H, s, NH, D$_2$O exchg.), 7.25-7.44 (2H, m, Ar—H), 7.78 (1H, s, =CH), 9.18 (1H, s, —CONH, D$_2$O exchg.); MS: m/z=392.40 [M+1]+; Analysis for C$_{23}$H$_{25}$N$_3$O$_3$: C (70.57) H (6.44) N (10.73) %; found C (70.77) H (6.43) N (10.71)%.

Compound N-13 4-(4-Ethoxyphenyl)-5-[4-(piperidin-1-yl) benzoyl]-3,4-dihydropyrimidin-2(1H)-one (N-13): Color: yellow; Yield: 55%; M.p.: 200-202° C.; UV λmax (Methanol)=444 nm; IR (KBr) cm-1:3270 (N—H), 2800 (ArC—H), 1672 (C=O), 1631 (C=O), 1600 (C=C); 1H NMR (500 MHz, DMSO-d6): δ=1.30 (3H, t, J=7.0 Hz, CH3), 1.57 (8H, s, 4×—CH2, piperidine), 2.74 (1H, s, —CH, piperidine), 2.89 (1H, s, —CH, piperidine), 3.98 (2H, q, J=9.0 Hz, —OCH2), 5.38 (1H, s, H-4), 6.86-6.93 (4H, m, Ar—H), 6.97 (1H, s, NH, $D_2O$ exchg.), 7.20 (4H, m, Ar—H), 7.69 (1H, s, =CH), 9.11 (1H, s, —CONH, $D_2O$ exchg.); 13C NMR (125.76 MHz, DMSO-d6): δ=15.1, 24.0, 25.3, 48.0, 50.0, 65.0, 111.5, 113.2, 130.9, 131.9, 132.8, 154.6, 158.0, 162.0, 190.3; MS: m/z=405.00 [M]+; Analysis for $C_{24}H_{27}N_3O_3$: C (71.09) H (6.71) N (10.36)%; found C (71.34) H (6.72) N (10.34)%.

Compound N-14 4-(2,4,5-Trimethoxyphenyl)-5-[4-(piperidin-1-yl) benzoyl]-3,4-dihydropyrimiden-2(1H)-one (N-14): Color: brown; Yield: 60%; M.p.:155-157° C.; UV λmax (Methanol)=449 nm; IR (KBr) cm−1: 3300 (N—H), 2800 (ArC—H), 1701 (C=O), 1686 (C=O), 1654 (C=C); 1H NMR (500 MHz, DMSO-d6): δ=1.57 (8H, s, 4×—$CH_2$, piperidine), 2.70 (1H, s, —CH, piperidine), 2.80 (1H, s, —CH, piperidine), 3.71 (9H, s, 3×—OCH3), 5.62 (1H, s, H-4), 6.74-6.96 (6H, m, Ar—H), 7.0 (1H, s, NH, $D_2O$ exchg.), 7.50 (1H, s, =CH), 9.20 (1H, s, —CONH, $D_2O$ exchg.); 13C NMR (125.76 MHz, DMSO-d6): δ=15.0, 19.1, 24.5, 25.3, 48.0, 48.5, 50.0, 56.2, 60.6, 61.3, 65.3, 108.1, 114.4, 113.2, 113.5, 123.5, 127.6, 129.8, 130.5, 132.6, 142.0, 151.5, 153.3, 153.5, 190.1; MS: m/z=451.00 [M]+; Analysis for $C_{25}H_{29}N_3O_5$: C C (66.50) H (6.47) N (9.31)%; found C (66.70) H (6.48) N (9.33)%.

Compound N-15 4-(2,3,4-Trimethoxyphenyl)-5-[4-(piperidin-1-yl) benzoyl]-3,4-dihydropyrimidin-2(1H)-one (N-15): Color: brown; Yield: 57%; M.p.:125-127° C.; UV λmax (Methanol)=441 nm; IR (KBr) cm$^{-1}$: 3478 (N—H), 2852 (ArC—H), 1634 (C=O), 1596 (C=O), 1567 (C—C); 1H NMR (500 MHz, DMSO-d6); δ=1.56 (8H, s, 4×—$CH_2$, piperidine), 2.70 (1H, s, —CH, piperidine),2.80 (1H, s, —CH, piperidine), 3.70 (9H, s, 3×—OCH3), 5.64 (1H, s, H-4), 6.75-6.97 (6H, m, Ar—H), 7.0 (1H, s, NH, $D_2O$ exchg.), 7.44 (1H, s, —CH), 9.20 (1H, s, —CONH, $D_2O$ exchg.); 13C NMR (125.76 MHz, DMSO-d6): δ=15.6, 19.0, 24.4, 25.3, 48.0, 48.5, 49.8, 56.2, 60.6, 61.3, 65.3, 108.1, 112.4, 113.2, 113.8, 123.0, 127.4, 129.9, 130.6, 132.3, 142.0, 151.5, 153.3, 153.5, 190.4; MS: m/z452.08 [M+1]+; Analysis for $C_{25}H_{29}N_3O_5$: C (66.50) (6.47) N (9.31)%; found C (66.30) H (6.46) N (9.29)%.

Compound N-16 4-(3,4,5-Trimethoxyphenyl)-5-[4-(piperidin-1-yl) benzoyl]-3,4-dihydropyrimidin-2(1H)-one (N-16): Color: brown; Yield: 60%; M.p.: 135-137° C.; UV λmax (Methanol)=441 nm; IR (KBr) cm$^{-1}$: 3236 (N—H), 2933 (ArC—H), 1701 (C=O), 1650 (C=O), 1610 (C=C); 1H NMR (500 MHz, DMSO-d6): δ=1.55 (8H, s, 4×—$CH_2$, piperidine), 2.70 (1H, s, —CH, piperidine), 2.80 (1H, s, —CH, piperidine), 3.6 (9H, s, 3×—OCH3), 5.40 (1H, s, H-4), 6.65-6.93 (6H, m, Ar—H), 7.0 (1H, s, NH, $D_2O$ exchg.), 7.5 (1H, s, =CH), 9.2 (1H, s, —CONH, $D_2O$ exchg.); 13C NMR (125.76 MHz, DMSO-d6): δ=19.5, 24.4, 25.2, 25.3, 47.9, 48.5, 54.1, 56.2, 60.3, 65.3, 104.1, 112.4, 113.8, 127.2, 130.7, 137.2., 140.1, 152.9, 153.3, 153.6, 190.6; MS: m/z=452.40 [M+1] ; Analysis for $C_{25}H_{29}N_3O_5$: C (66.50) H (6.47) N (9.31)%; found C (66.70) H (6.48) N (9.32)%.

Compound N-17 4-(2,4,6-Trimethoxyphenyl)-5-[4-(piperidin-1-yl) benzoyl]-3,4-dihydropyrimidin-2(1H)-one (N-17): Color: brown; Yield: 60%; M.p.: 140-142° C.; UV λmax (Methanol)=428 nm; IR (KBr) cm$^{-1}$: 3300 (N—H), 2930 (ArC—H), 1685 (C=O), 1654 (C=O), 1595 (C=C); 1H NMR (500 MHz, DMSO-d6): δ=1.54 (8H, s, 4×—$CH_2$, piperidine), 2.7 (1H, s, —CH, piperidine), 2.80 (1H, s, —CH, piperidine), 3.70 (9H, s, 3×—OCH3), 5.79 (1H, s, H-4), 6.90-6.93 (6H, m, Ar—H), 7.0 (1H, s, NH, $D_2O$ exchg.), 7.51 (1H, s, =CH), 9.21 (1H, s, —CONH, $D_2O$ exchg.); 13C NMR (125.76 MHz, DMSO-d6): δ=15.6, 19.0, 24.4, 25.3, 48.0, 48.5, 49.5, 56.0, 56.5, 60.6, 65.4, 112.4, 112.5, 113.8, 120.2, 124.3, 127.3, 130.7, 130.9, 137.6, 139.5, 146.5, 151.8, 152.9, 153.5, 190.3; MS: m/z=453.92 [M+2]+; Analysis for $C_{25}H_{29}N_3O_5$: C (66.50) H (6.47) N (9.31)%; found C (66.35) H (6.46) N (9.30)%.

Compound N-18 4-(2,4-Dimethoxyphenyl)-5-[4-(piperidin-1-yl) benzoyl]-3,4-dihydropyrimiden-2(1H)-one (N-18): Color: brown; Yield: 55%; M.p.: 135-137° C.; UV λmax (Methanol)=419 nm; IR (KBr) cm−1: 3270 (N—H), 2900 (ArC—H), 1670 (C=O), 1635 (C=O), 1621 (C=C); 1H NMR (500 MHz, DMSO-d6): δ=1.57 (8H, s, 4×—$CH_2$, piperidin), 2.70 (1H, s, —CH, piperidine), 2.80 (1H, s, —CH, piperidine), 3.83 (6H, s, 2×—OCH3), 5.64 (1H, s, H-4), 6.44-6.93 (7H, m, Ar—H), 7.0 (1H, s, NH, D2O exchg.), 8.0 (1H, s, =CH), 9.07 (1H, s, —CONH, $D_2O$ exchg.); 13C NMR (125.76 MHz, DMSO-d6): δ=15.6, 24.4, 25.3, 48.0, 48.5, 49.3, 55.6, 55.9, 65.4, 99.1, 104.8, 111.7, 113.2, 113.2, 124.0, 127.4, 128.6, 130.7, 132.8, 139.6, 152.2, 153.5, 158.3, 160.4, 190.4; MS: m/z=421.67 [M]+; Analysis for: C (68.39) H (6.46) N (9.97)%; found C (66.45) H (6.47) N (9.95)%.

EXAMPLE 2

Evaluation of Anti-Ulcer Activity and Gastric Secretion in Rats

Albino Wistar rats of either sex, approximately the same age, weighing 150 to 200 g and fed on a diet of standard chow were used in this study. They were randomly divided into experimental groups of six rats each. Compounds (N-1 to N-18) 12.5, 25, and 50 mg/kg were given orally in the anti-ulcer studies and intraperitoneally for gastric secretion evaluation. The rats were sacrificed, and the stomachs removed and opened along the greater curvature, After washing with saline, the gastric lesions were quantified by a person unaware of the treatments. The animal study protocol was approved by the Research and Ethics Committee of the Experimental Animal Care Society, College of Pharmacy, King Saud University, Riyadh, Saudi Arabia.

Gastric lesions induced by ethanol: Albino rats of either sex weighing between (150-200 g) are divided into groups. The animals were fasted for 24 hours with free access to water. Animals were given test drugs or standard drug. One hour later 1 mL/200 gm of 80% ethanol is administered orally to each animal. The animals were anaesthetized 1 hour latter with anesthetic ether and stomach was incised along the greater curvature and ulceration was scored. The number of ulcers and the length of each ulcer were measured. Ulcer index was calculated using severity scores. The mucosal damage was examined by means of a magnifying glass. For each stomach the mucosal damage was assessed according to the following scoring system: 0.5 redness; 1.0 spot ulcers; 1.5 hemorrhagic streaks; 2.0 ulcers<3, but≤5; 3.0 ulcers>5. Table 1 provides the effect of compounds on gastric lesions induced by 80% ethanol (mean±SE).

TABLE 1

Effect on Gastric Lesions Induced by 80% Ethanol

| | 80% EtOH | Ranitidine 50 (mg/kg) | | Compounds 12.5 (mg/kg) | | 25 (mg/kg) | | 50 (mg/kg) | |
|---|---|---|---|---|---|---|---|---|---|
| C | Mean ± SE | Mean ± SE | % change | Mean ± SE | % change | Mean ± SE | % change | Mean ± SE | % change |
| N-1 | 7.5 ± 0.28 | 1.75 ± 0.47*** | 76.66 | 7.25 ± 0.47 | — | 6.75 ± 0.25 | — | 6.25 ± 0.47* | — |
| N-2 | 7.00 ± 0.40 | 2.00 ± 0.40*** | 71.42 | 6.0 ± 0.16 | 14.2 | 3.50 ± 0.28* | 21.4 | 5.00 ± 0.16** | 28.5 |
| N-3 | 7.50 ± 0.28 | 2.00 ± 0.40 | 73.3 | 5.0 ± 0.40*** | 33.33 | 3.5 ± 0.2** | 53.3 | 3.00 ± 0.4*** | 60.0 |
| N-4 | 6.75 ± 0.25 | 2.25 ± 0.47*** | 66.6 | 6.75 ± 0.25 | — | 5.50 ± 0.4 | — | 6.25 ± 0.25 | 7.40 |
| N-5 | 7.0 ± 0.40 | 2.0 ± 0.4*** | 71.4 | 7.0 ± 0.4 | — | 6.5 ± 0.28 | 7.1 | 6.25 ± 0.47 | 10.7 |
| N-6 | 7.0 ± 0.40 | 2.5 ± 0.28*** | 64.2 | 7.25 ± 0.25 | — | 6.5 ± 0.2 | 7.1 | 6.25 ± 0.25 | 10.7 |
| N-7 | 7.5 ± 0.28 | 2.75 ± 0.25*** | 63.3 | 6.75 ± 0.25 | 10 | 5.5 ± 0.2*** | 26.6 | 5.0 ± 0.4*** | 33.3 |
| N-8 | 7.5 ± 0.28 | 2.2 ± 0.4*** | 70 | 5.0 ± 0.4*** | 33.3 | 3.7 ± 0.4*** | 50 | 3.5 ± 0.2*** | 53.3 |
| N-9 | 7.0 ± 0.4 | 2.2 ± 0.6*** | 67.8 | 7.2 ± 0.25 | — | 6.5± | 2 | 6.0 ± 0.4 | — |
| N-10 | 7.0 ± 0.4 | 2.0 ± 0.5*** | 71.4 | 6.0 ± 0.4 | 14 | 5.75 ± 0.2* | 17.8 | 5.5 ± 0.2* | 21.4 |
| N-11 | 7.7 ± 0.25 | 1.7 ± 0.4*** | 77.4 | 6.0 ± 0.4** | 22.5 | 4.0 ± 0.1*** | 48.3 | 3.0 ± 0.4*** | 61.2 |
| N-12 | 7.0 ± 0.4 | 2.7 ± 0.2*** | 60.7 | 7.0 ± 0.4 | — | 6.5 ± 0.2 | 7.1 | 6.25 ± 0.4 | 10.7 |
| N-13 | 7.0 ± 0.40 | 1.7 ± 0.4*** | 75 | 7.0 ± 0.4 | — | 6.5 ± 0.2 | 7.1 | 6.0 ± 0.4 | 14.2 |
| N-14 | 7.2 ± 0.25 | 1.70.4*** | 75.8 | 6.5 ± 0.2 | 10.3 | 5.25 ± 0.4** | 27.5 | 4.5 ± 0.2*** | 37.9 |
| N-15 | 7.7 ± 0.2 | 2.5 ± 0.2*** | 67.7 | 5.0 ± 0.4*** | 35.4 | 3.5 ± 0.2*** | 54.8 | 2.5 ± 0.2*** | 67.7 |
| N-16 | 7.0 ± 0.4 | 2.0 ± 0.4*** | 71.4 | 6.5 ± 0.2 | 7.1 | 5.75 ± 0.4 | 17.8 | 5.5 ± 0.2* | 21.4 |
| N-17 | 7.2 ± 0.2 | 2.75 ± 0.2*** | 62 | 7.00 ± 0.4 | — | 5.2 ± 0.4** | 27.5 | 4.5 ± 0.4*** | 37.9 |
| N-18 | 7.7 ± 0.2 | 2.0 ± 0.4*** | 74.1 | 7.2 ± 0.2 | 6.4 | 6.5 ± 0.2* | 16.1 | 6.0 ± 0.4** | 22.5 |

Notes:
C = Compound

Gastric lesions induced by necrotizing agents (cytoprotection): Each rat was administered 1 ml of a necrotizing agent (80% ethanol, 0.2 mol/L NaOH or 25% NaCl). Compounds (N-3, N-8, N-11, and N-15) were given 30 minutes before the administration of necrotizing agents. One hour after the administration of ethanol and the alkalis, the rats were sacrificed and examined for stomach lesions.

The scoring of stomach lesions was as follows: patchy lesions of the stomach induced by ethanol were scored according to the method described using the following scale: 0=normal mucosa; 1=hyperemic mucosa or up to 3 small patches; 2=from 4 to 10 small patches; 3=more than 10 small or up to 3 medium-sized patches; 4=from 4 to 6 medium-sized patches; 5=more than 6 medium-sized or up to 3 large patches; 6=from 4 to 6 large patches; 7=from 7 to 10 large patches; 8=more than 10 large patches or extensive necrotic zones. "small" was defined as up to 2 mm across (max. diameter), "medium-sized" between 2 and 4 mm across and "large" more than 4 mm across. Table 2 provides the effect of compounds on gastric lesions induced by necrotizing agents (mean±SE).

TABLE 2

Effect on Gastric Lesions Induced by Necrotizing Agents

| Treatment | Dose (mg/kg, i.p) | 80% EtOH | Ulcer Index 0.2 mol/L NaOH | 25% NaCl |
|---|---|---|---|---|
| Control | 1 mL | 7.66 ± 0.21 | 7.33 ± 0.21 | 6.83 ± 0.30 |
| Ranitidine (Standard) | 50 | 1.50 ± 0.22*** | 1.00 ± 0.36*** | 1.16 ± 0.30*** |
| N-3 | 12.5 | 6.83 ± 0.30* | 4.50 ± 0.22.*** | 5.16 ± 0.47* |
| N-3 | 25 | 4.16 ± 0.30*** | 2.66 ± 0.33*** | 2.83 ± 0.30*** |
| N-3 | 50 | 3.00 ± 0.36*** | 1.83 ± 0.40*** | 1.66 ± 0.33*** |
| N-8 | 12.5 | 7.00 ± 0.36 | 6.66 ± 0.33 | 6.00 ± 0.25 |
| N-8 | 25 | 6.50 ± 0.42* | 5.33 ± 0.71* | 5.00 ± 0.44** |
| N-8 | 50 | 5.83 ± 0.30*** | 3.83 ± 0.30*** | 3.33 ± 0.30*** |
| N-11 | 12.5 | 7.16 ± 0.30 | 6.33 ± 0.42 | 6.00 ± 0.36 |
| N-11 | 25 | 6.16 ± 0.30** | 3.66 ± 0.21*** | 4.83 ± 0.40** |
| N-11 | 50 | 4.83 ± 0.30*** | 3.66 ± 0.33*** | 3.83 ± 0.30*** |
| N-15 | 12.5 | 4.66 ± 0.33*** | 3.50 ± 0.22*** | 3.66 ± 0.33*** |
| N-15 | 25 | 2.66 ± 0.33*** | 2.16 ± 0.30*** | 2.66 ± 0.33*** |
| N-15 | 50 | 2.16 ± 0.30*** | 1.33 ± 0.42*** | 1.66 ± 0.33*** |

Notes:
Six rats were used in each group.
*p < 0.005, p < 0.01, *p < 0.001 vs control group, student's t-test.

Gastric lesions induced by Indomethacin: Indomethacin was suspended in 1.0% carboxymethylcellulose (CMC) in water (6 mg/mL) and administered orally to the 36 hour fasted rats at a dose of 30 mg/kg body weight. Control rats were treated similarly with an equivalent amount of vehicle. Compounds (N-3, N-8, N-11, and N-15) were given 30 minutes prior to Indomethacin administration at a dose of 12.5, 2.5, and 50 mg/kg. The animals were sacrificed 6 hours after treatment. The stomachs were excised, rinsed with normal saline and examined for ulceration. Table 3 provides the effect of compounds on Indomethacin-induced gastric mucosal lesions (mean±SE).

TABLE 3

Effect on indomethacin-Induced Gastric Mucosal Lesions

| Treatment | Dose (mg/kg, i.p) | Ulcer Index |
|---|---|---|
| Control (Indomethacin) | 30 | 35.66 ± 1.05 |
| Ranitidine (Standard) | 50 | 8.50 ± 0.56*** |
| N-3 | 12.5 | 29.83 ± 1.66* |
| N-3 | 25 | 20.50 ± 1.52*** |
| N-3 | 50 | 12.66 ± 1.28*** |
| N-8 | 12.5 | 33.00 ± 1.52 |
| N-8 | 25 | 29.50 ± 1.58* |
| N-8 | 50 | 28.66 ± 1.45** |
| N-11 | 12.5 | 33.00 ± 1.03 |

TABLE 3-continued

Effect on indomethacin-Induced Gastric Mucosal Lesions

| Treatment | Dose (mg/kg, i.p) | Ulcer Index |
|---|---|---|
| N-11 | 25 | 30.66 ± 1.28* |
| N-11 | 50 | 28.31 ± 1.78** |
| N-15 | 12.5 | 26.33 ± 1.30*** |
| N-15 | 75 | 21.50 ± 1.33*** |
| N-15 | 50 | 14.50 ± 1.64*** |

Notes:
Six rats were used in each group.
*p < 0.05, p < 0.01, *p < 0.001 vs control (indomethacin only) group, student's t-test.

Hypothermic restraint stress-induced ulcers: Animals were fasted for 36 hours but had access to water ad libitum. Thirty minutes after the oral administration of compounds (N-3, N-8, N-11, and N-15) 12.5, 25, and 50 mg/kg, the rats were immobilized in restraint cages and placed inside a ventilated refrigerator maintained at 3±1° C. for 3 hours. The animals were then sacrificed and the stomachs were excised. They were examined for ulceration and the severity of intraluminal bleeding according to the following arbitrary scale. 0=no blood detectable; 1=thin blood follows the rugae; 2=thick blood follows the rugae; 3=thick blood follows the rugae with blood clots in certain areas; and 4=extensive covering of the whole gastric mucosal surface with thick blood. Table 4 provides the effect of compounds on hypothermic restraint stress-induced intraluminal bleeding and gastric lesion in rats (mean±SE).

TABLE 4

Effect on Hypothermic Restraint Stress-Induced Intraluminal Bleeding and Gastric Lesion in Rats

| Treatments n = 6 | Dose (mg/kg, i.p) | Intraluminal Bleeding Score | Gastric Lesion Ulcer Index |
|---|---|---|---|
| Control | — | 4.16 ± 0.30 | 33.00 ± 1.26 |
| Ranitidine (Standard) | 50 | 0.83 ± 0.30*** | 9.66 ± 0.95*** |
| N-3 | 12.5 | 2.83 ± 0.30* | 24.16 ± 1.70** |
| N-3 | 25 | 1.50 ± 0.22*** | 17.66 ± 0.76*** |
| N-3 | 50 | 1.16 ± 0.30*** | 13.83 ± 0.60*** |
| N-8 | 12.5 | 3.50 ± 0.42 | 29.83 ± 1.50 |
| N-8 | 25 | 3.33 ± 0.21* | 27.66 ± 1.60* |
| N-8 | 50 | 2.50 ± 0.42* | 18.66 ± 0.55*** |
| N-11 | 12.5 | 3.66 ± 0.33 | 29.83 ± 1.51 |
| N-11 | 75 | 2.66 ± 0.33** | 29.00 ± 1.21* |
| N-11 | 50 | 2.00 ± 0.36*** | 21.00 ± 0.51*** |
| N-15 | 12.5 | 2.16 ± 0.30*** | 25.66 ± 1.08** |
| N-15 | 25 | 1.66 ± 0.21*** | 16.66 ± 0.33** |
| N-15 | 50 | 1.33 ± 0.33*** | 12.33 ± 0.84*** |

Notes:
Six rats were used in each group.
*p < 0.05, p < 0.01, *p < 0.001 vs control (indomethacin only) group, student's t-test.

Pylorus-ligated rats: Rats were fasted for 36 hours with access to water ad libitum before pylorus ligation under ether anesthesia was carried out. Care was taken not to cause bleeding or to occlude blood vessels. Compounds (N-3, N-8, N-11, and N-15) were administered intraperitoneally immediately after pylorus ligation. The rats were sacrificed at 6 hours after pylorus ligation. The stomachs were removed, the contents were collected, volumes measured, centrifuged and analyzed for tritratable acidity against 0.01 mol/h, NaOH at pH 7.0. Table 5 provides the effect of compounds on gastric secretion, acidity, and gastric lesion index in pylorus-ligated Shay rats (mean±SE).

TABLE 5

Effect on Gastric Secretion, Acidity, and Gastric Lesion Index in Pylorus-ligated Shay Rats

| Treatment | Dose (mg/kg, i.p.) | Volume of Gastric Content (mL) | Titratable Acidity (mEg/L) | Ulcer Index |
|---|---|---|---|---|
| Control | — | 11.23 ± 0.18 | 173.88 ± 5.12 | 3.33 ± 0.21 |
| Ranitidine (Standard) | 50 | 4.06 ± 0.18*** | 58.88 ± 1.85*** | 0.50 ± 0.22*** |
| N-3 | 12.5 | 9.03 ± 0.24*** | 153.88 ± 5.40* | 2.33 ± 0.33* |
| N-3 | 25 | 6.31 ± 0.25*** | 97.77 ± 2.93*** | 1.83 ± 0.304* |
| N-3 | 50 | 4.63 ± 0.22*** | 84.84 ± 2.38*** | 1.16 ± 0.30*** |
| N-8 | 12.5 | 10.50 ± 0.34 | 161.11 ± 4.36 | 3.16 ± 0.30 |
| N-8 | 25 | 9.36 ± 1.22** | 133.33 ± 3.22*** | 2.50 ± 0.22* |
| N-8 | 50 | 6.46 ± 0.16*** | 115.00 ± 5.75*** | 2.00 ± 0.13* |
| N-11 | 12.5 | 10.20 ± 0.29* | 160.55 ± 3.48 | 2.83 ± 0.30 |
| N-11 | 25 | 7.35 ± 0.19*** | 141.11 ± 6.30** | 2.50 ± 0.42 |
| N-11 | 50 | 6.63 ± 0.21*** | 116.66 ± 4.63*** | 2.33 ± 0.71** |
| N45 | 12.5 | 6.68 ± 0.18*** | 116.11 ± 2.64*** | 1.83 ± 0.304* |
| N45 | 25 | 5.50 ± 0.24*** | 86.11 ± 3.98*** | 1.50 ± 0.22*** |
| N-15 | 50 | 4.76 ± 0.23*** | 73.33 ± 2.43*** | 1.00 ± 0.36*** |

Notes:
Six rats were used in each group.
*p < 0.05, p < 0.01, *p < 0.0001 control (distilled water) group, student's t-test.

Determination of gastric wall mucus (GWM): Gastric wall mucus was determined according to the modified procedure. The glandular segment of the stomach was separated from the rumen of the stomach, weighed, and transferred immediately to 10 mL of 0.1% w/v Alcian blue solution (in 0.16 mmol/L sucrose solution buffered with 0.05 mL sodium acetate at pH 5. Tissue was stained for 2 hours in Alcian blue, and excess dye was removed by two successive rinses with 10 mL of 0.25 mmol/L sucrose, firstly after 15 minutes and then after 45 minutes. Dye complexed with the gastric wall mucus was extracted with 10 ml of 0.5 mmol/L magnesium chloride which was intermittently shaken for 1 minute at 30 minute intervals for 2 hours. Four milliliters of blue extract were then vigorously shaken with an equal volume of diethyl ether. The resulting emulsion was centrifuged at 4000 r/min for 10 minutes and the absorbance of the aqueous layer was recorded at 580 nm. The quantity of Alcian blue extracted per gram of wet glandular tissue was then calculated. Table 6 provides the effect of compounds on the change in gastric wall mucus in stomach tissue induced by 80% ethanol (mean±SE).

TABLE 6

Effect on Gastric Wall Mucus

| Treatment | Dose (mg/kg, i.p) | Gastric Wall Mucus (mean ± SE, µg/g) |
|---|---|---|
| Control (Normal) | — | 276.53 ± 10.19 |
| 80% EtOH | 1 mL | 201.91 ± 8.32***[a] |
| Ranitidine (Standard) | 50 | 287.24 ± 10.70***[b] |
| N-3 | 12.5 | 242.08 ± 4.03*[b] |
| N-3 | 25 | 241.66 ± 6.91**[b] |
| N-3 | 50 | 256.18 ± 8.39***[b] |
| N-8 | 12.5 | 206.39 ± 7.18[b] |
| N-8 | 25 | 212.00 ± 6.40[b] |
| N-8 | 50 | 244.65 ± 5.36**[b] |
| N-11 | 12.5 | 192.87 ± 12.84[b] |
| N-11 | 25 | 224.88 ± 4.64*[b] |
| N-11 | 50 | 217.36 ± 3.31**[b] |
| N-15 | 12.5 | 231.78 ± 4.77*[b] |

TABLE 6-continued

Effect on Gastric Wall Mucus

| Treatment | Dose (mg/kg, i.p) | Gastric Wall Mucus (mean ± SE, µg/g) |
|---|---|---|
| N-15 | 25 | 248.09 ± 7.69**[b] |
| N-15 | 50 | 275.32 ± 5.37***[b] |

Notes:
Six rats were used in each group.
*p < 0.05, p < 0.01, *p < 0.001 control (80% Ethanol only) group, student's t-test.
[a] as compared to the control group
[b] as compared to the 80% ethanol only group Estimation of non-protein sulfhydryls (NP—SH): Gastric mucosal non-protein sulfhydryls were measured according to the method. The glandular part of the stomach was homogenized in ice-cold 0.02 mmol/L ethylenediaminetetraacetic acid (EDTA). Aliquots of 5 mL of the homogenates were mixed in 15 mL test tubes with 4 mL of distilled water and 1 mL of 50% trichloroacetic acid (TCA). The tubes were shaken intermittently for 10 minutes and centrifuged at 3000 r/min. Two milliliters of supernatant were mixed with 4 mL of 0.4 mol/L Tris buffer at pH 8.9. Then 0.1 ML of 5, 5'-dithio-bis (2-nitrobenzoic acid) (DTNB) was added and the sample was shaken. The absorbance was measured within 5 minutes of DTNB addition at 412 nm against a reagent blank.

Determination of malondialdehyde (MDA): The animals were sacrificed 1 hour after ethanol administration. The stomachs were removed and each was homogenized in 0.15 mol/L KCl (at 4° C.) in a Potter-Elvehjem type C homogenizer to give a 10% w/v homogenate. Aliquots of homogenate 1 mL in volume were incubated at 37° C. for 3 hours in a metabolic shaker. Then 1 mL of 10% aqueous TCA was added and mixed. The mixture was then centrifuged at 800 g for 10 minutes. One milliliter of the supernatant was removed and mixed with 1 mL of 0.67% w/v thiobarbituric acid in water and placed in a boiling water bath for 10 minutes. The mixture was cooled and diluted with 1 mL distilled water. The absorbance of the solution was then read at 535 nm. The content of malondialdehyde (nmol/g wet tissue) (index of the magnitude of lipid peroxidation) was then calculated, by reference to a standard curve of malondialdehyde solution. Table 7 provides the effect of compounds on the levels of MDA, NP—SH, and total protein in stomach tissue induced by 80% ethanol (mean±SE).

TABLE 7

Effect on MDA, NP-SH, and Total Protein Levels

| Treatment | Dose | MDA (nmol/g) | NP-SH (nmol/g) | Total Protein (g/L) |
|---|---|---|---|---|
| Control (Normal) | — | 1.14 ± 0.06 | 5.03 ± 0.10 | 122.55 ± 3.23 |
| 80% EtOH | 1 mL | 7.42 ± 0.30***[a] | 3.22 ± 0.20***[a] | 47.50 ± 2.08***[a] |
| Ranitidine (Standard) | 50 | 1.65 ± 0.02***[b] | 4.24 ± 0.15**[b] | 104.59 ± 1.59***[b] |
| N-3 | 12.5 | 4.47 ± 0.44***[b] | 3.15 ± 0.20[b] | 58.68 ± 3.19*[b] |
| N-3 | 25 | 3.07 ± 0.16***[b] | 4.23 ± 0.23**[b] | 74.65 ± 3.79*[b] |
| N-3 | 50 | 1.95 ± 0.05***[b] | 4.56 ± 0.17***[b] | 95.80 ± 1.51***[b] |
| N-8 | 12.5 | 6.63 ± 0.26[b] | 3.49 ± 0.16[b] | 45.90 ± 1.14[b] |
| N-8 | 25 | 4.83 ± 0.24***[b] | 3.61 ± 0.12[b] | 55.88 ± 1.71*[b] |
| N-8 | 50 | 3.75 ± 0.07***[b] | 4.61 ± 0.27**[b] | 66.26 ± 1.47*** |
| N-11 | 12.5 | 5.16 ± 0.22***[b] | 2.93 ± 0.11[b] | 53.89 ± 1.48*[b] |
| N-11 | 25 | 3.99 ± 0.17***[b] | 3.40 ± 0.18[b] | 64.27 ± 2.08***[b] |
| N-11 | 50 | 3.36 ± 0.08***[b] | 4.35 ± 0.11***[b] | 72.25 ± 1.43***[b] |
| N-15 | 12.5 | 3.51 ± 0.08***[b] | 3.38 ± 0.07[b] | 71.45 ± 1.43*[b] |
| N-15 | 25 | 2.72 ± 0.10***[b] | 4.29 ± 0.24**[b] | 81.43 ± 3.65***[b] |
| N-15 | 50 | 1.90 ± 0.06***[b] | 4.92 ± 0.30***[b] | 96.60 ± 1.18***[b] |

Notes:
Six rats were used in each groups.
*p < 0.05, p < 0.01, *p < 0.001 vs control (80% Ethanol only) group, student's t-test.
[a] as compared to the control group
[b] as compared to the 80% ethanol only group $LD_{50}$ determination: For each mouse, the observation was made for 24 hours and symptoms of toxicity and rate of mortality in each group were noted. At the end of the study period, expired animals were counted for the calculation of $LD_{50}$. The following arithmetic method from Karber (Arch. Exptl. Pathol. Pharmakol, 1963, 162, 480-483) was used for the determination of $LD_{50}$:

$$LD_{50} = LD_{100} - \Sigma \times (a \times b)/n$$

wherein n=total number of animals in a group; a=the difference between two successive doses of administered extract/substance; b=the average number of dead animals in two successive doses; and $LD_{100}$=lethal dose causing the 100% death of all test animals.

Table 8 provides the $LD_{50}$ values of the compounds determined by the Karber method.

TABLE 8

$LD_{50}$ Values Determined by the Karber Method

| Group | Dose mg/kg | No. of Animals | D.D (a) | Dead | M.M (b) | Pro.(a * b) |
|---|---|---|---|---|---|---|
| | | | N-3 | | | |
| 1 | 5 | 10 | | 0 | | |
| 2 | 25 | 10 | 20 | 0 | 0 | 0 |
| 3 | 50 | 10 | 25 | 2 | 1 | 25 |
| 4 | 100 | 10 | 50 | 5 | 3.5 | 175 |
| 5 | 200 | 10 | 100 | 8 | 6.5 | 650 |
| 6 | 300 | 10 | 100 | 10 | 9 | 900 |
| | | | | | Total Product | 1750 |
| | | | | | $LD_{50}$ = | 125 mg/kg |
| | | | N-8 | | | |
| 1 | 5 | 10 | | 0 | | |
| 2 | 25 | 10 | 20 | 2 | 1 | 20 |
| 3 | 50 | 10 | 25 | 6 | 4 | 100 |
| 4 | 100 | 10 | 50 | 9 | 7.5 | 375 |

TABLE 8-continued

| | | LD$_{50}$ Values Determined by the Karber Method | | | | |
|---|---|---|---|---|---|---|
| Group | Dose mg/kg | No. of Animals | D.D (a) | Dead | M.M (b) | Pro.(a * b) |
| 5 | 200 | 10 | 100 | 10 | 9.5 | 950 |
| 6 | 300 | 10 | 100 | 10 | 10 | 1000 |
| | | | | | Total Product LD$_{50}$ = | 2445 55.5 mg/kg |
| | | N-15 | | | | |
| 1 | 5 | 10 | | 0 | 0 | |
| 2 | 25 | 10 | 20 | 1 | 0.5 | 10 |
| 3 | 50 | 10 | 25 | 3 | 2 | 50 |
| 4 | 100 | 10 | 50 | 4 | 3.5 | 175 |
| 5 | 200 | 10 | 100 | 9 | 6.5 | 650 |
| 6 | 300 | 10 | 100 | 10 | 9.5 | 950 |
| | | | | | Total Product LD$_{50}$ = | 1835 116.5 mg/kg |

Notes:
D.D = Dose difference
M.M = Mean Mortality
Factor = Last lethal dose-(Total Product/no. of animals)

Histopathological evaluation: Gastric tissue samples were fixed in neutral buffered formalin for 24 hours. Sections of gastric tissue were histopathologically examined to study the ulcerogenic and/or anti-ulcerogenic activity of compounds (N-3, N-8, N-11, and N-15). The tissues were fixed in 10% buffered formalin and processed using a VIP tissue processor. The processed tissues were embedded in paraffin blocks and sections about 5 mm thick were cut using an American optical rotary microtome. These sections were stained with haematoxylin and eosin using routine procedures. The slides were examined microscopically for pathomorphological changes such as congestion, hemorrhage, edema, and erosions using an arbitrary scale for severity assessment of these changes (FIGS. 3-14).

Figure 15A:
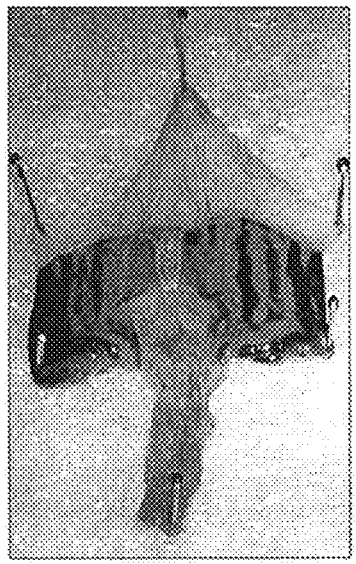
FIG. 15A illustrates the effect of 80% Ethanol on gastric mucosa.
Figure 15B:
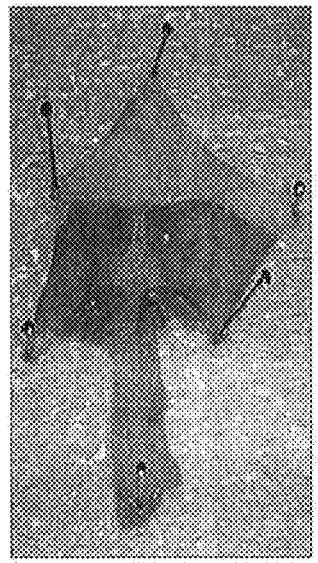
FIG. 15B illustrates the effect of Ranitidine (50 mg/kg) on gastric mucosa.
Figure 15C:
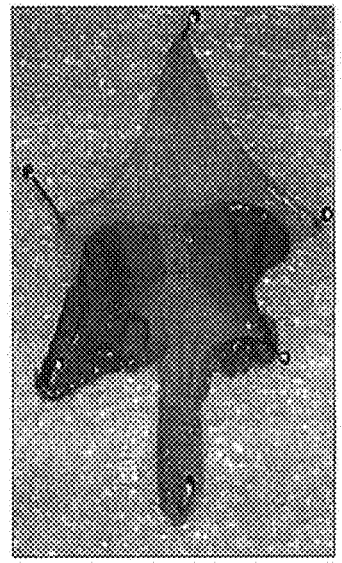
FIG. 15C illustrates the effect of Compound N-3 (50 mg/kg) on gastric mucosa.
Figure 15D:
FIG. 15D illustrates the effect of Compound N-8 (50 mg/kg) on gastric mucosa.
Figure 15E:
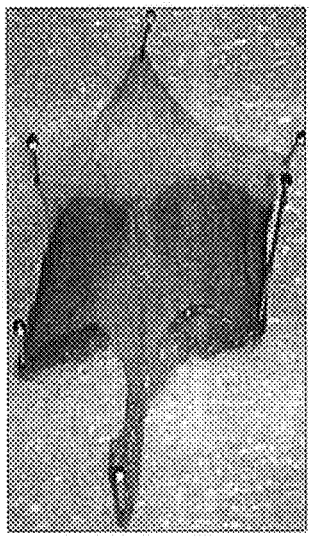
FIG. 15E illustrates the effect of Compound N-11 (50 mg/kg) on gastric mucosa.
Figure 15F:
FIG. 15F illustrates the effect of Compound N-15 (50 mg/kg) on gastric mucosa.

Furthermore, FIG. 15A shows a gastric section of rats treated with 80% Ethanol only, showing mucosal ulceration. FIG. 15B shows a gastric section of rats treated with Ranitidine (50 mg/kg) showing normal mucosa. FIG. 15C shows a gastric section of rats treated with compound N-3 (50 mg/kg) showing intact mucosa with mild ulceration. FIG. 15D shows a gastric section of rats treated with compound N-8 (50 mg/kg) showing intact normal mucosa, FIG. 15E shows a gastric section of rats treated with compound N-11 (50 mg/kg) showing intact normal mucosa. FIG. 15F shows a gastric section of rats treated with compound N-15 (50 mg/kg) showing intact normal mucosa.

Statistical analysis: Values in tables and figures are given as mean±SE. Data were analyzed by using one-way analysis of variance (ANOVA) followed by Student's t-test.

Biological evaluation of the compounds of Formula 1 of the present subject matter revealed that the compounds possess remarkable anti-ulcer activity. The results clearly point to the discovery of a new group of anti-ulcer agents. Compounds of Formula 1 can be used as anti-ulcer agents to produce effects comparable to those of the anti-ulcer drug Ranitidine.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

It is to be understood that the present subject matter is not limited to the embodiments described above, but encompasses any and all embodiments within the scope of the following claims.

We claim:
1. A dihydropyrimidinone derivative comprising a compound of Formula 1:

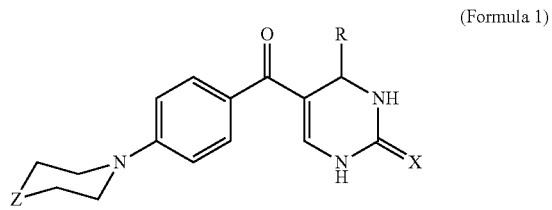

(Formula 1)

wherein
Z is selected from CH$_2$, O, and N;
X is selected from O and S; and
R represents aryl, substituted aryl, heteroaryl, or substituted heteroaryl,
wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and to pharmaceutically acceptable salts thereof.

2. The dihydropyrimidinone derivative of claim 1, wherein R is selected from the group consisting of 2-nitro phenyl, 3-nitro phenyl, 4-nitro phenyl, 4-chloro phenyl, 2,4-dichloro phenyl, 3,4-dimethoxy phenyl, 2-methoxy phenyl, 4-hydroxy phenyl, 3-hydroxy phenyl, dimethylamino phenyl, 3-methoxy phenyl, 4-ethoxy phenyl, 2,4,5- trimethoxy phenyl, 2,3,4-trimethoxy phenyl, 3,4,5-trimethoxy phenyl, 2,4,6-trimethoxy phenyl, and 2,4-dimethoxy phenyl.
3. The dihydropyrimidinone derivative of claim 1, wherein the compound is selected from the group consisting of:
N-1
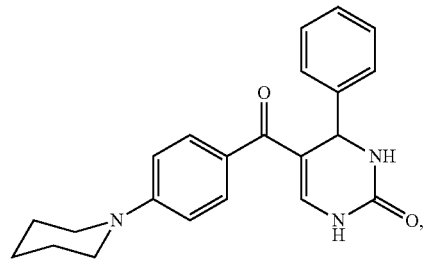
N-2
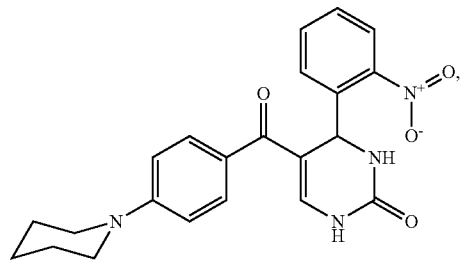
N-3
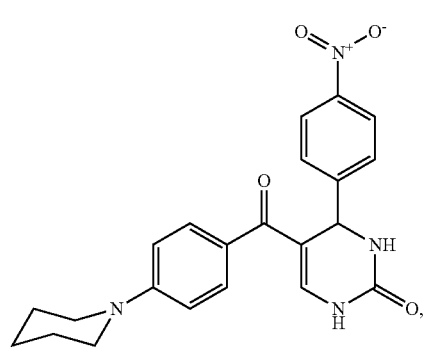
N-4
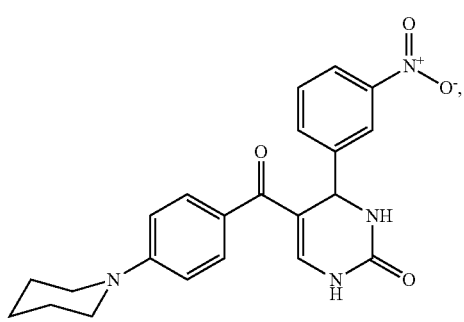
-continued
N-5
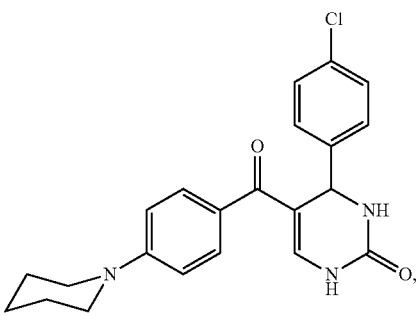
N-6
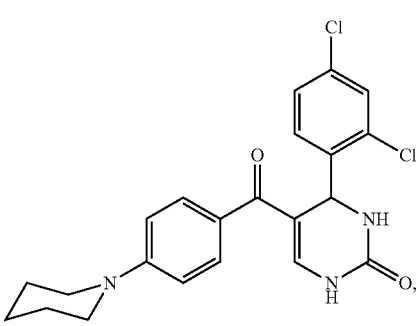
N-7
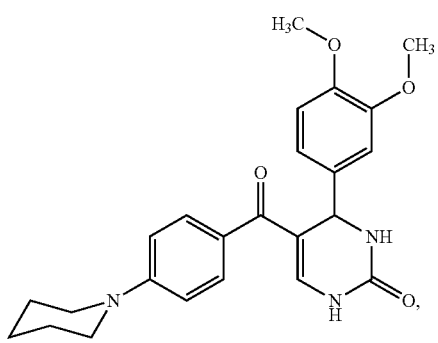
N-8
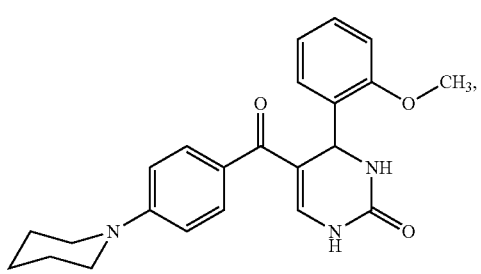
N-9
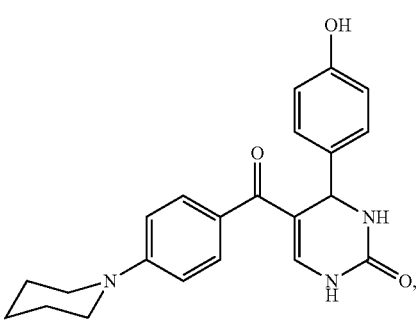

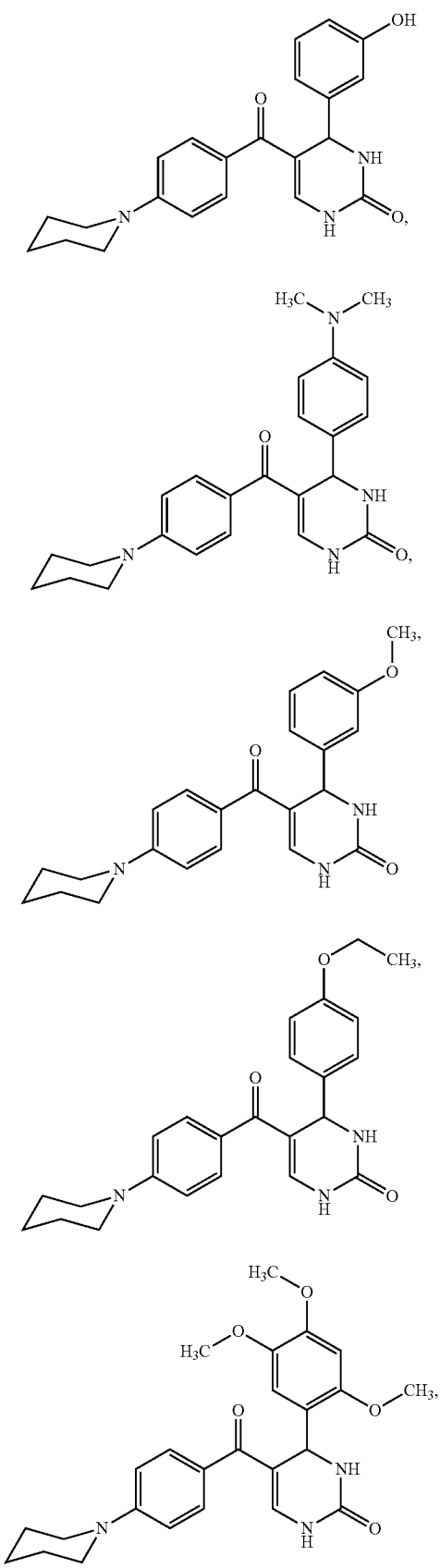
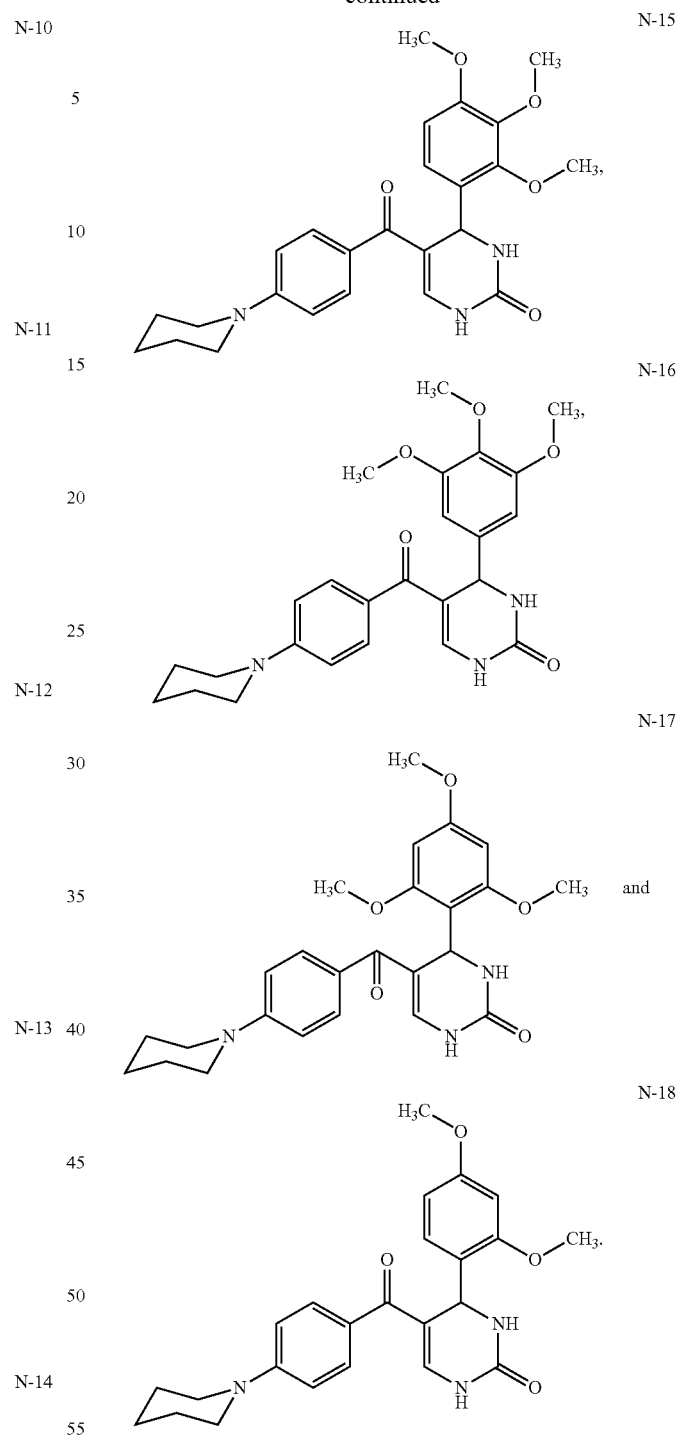

4. The dihydropyrimidinone derivative of claim 1, wherein the compound is an anti-ulcer agent.

5. A method of treating a gastrointestinal disease, comprising:
   administering to a patient in need thereof at least one compound of claim 1.

6. The method of claim 5, wherein the gastrointestinal disease is one of gastric ulcer, gastroesophagal reflux, and Zollinger-Elisson syndrome.

7. A pharmaceutical composition comprising:
   the dihydropyrimidinone derivative of claim 1; and
   a pharmaceutically acceptable carrier.

8. The pharmaceutical composition of claim 7, wherein the pharmaceutical composition is in a unit dosage form.

9. The pharmaceutical composition of claim 8, wherein the unit dosage form is a tablet, pill, capsule, granule, powder, ointment, sterile parenteral solution or suspension, metered aerosol or liquid spray, drops, ampule, injection, teaspoonful, or suppository.

10. A method of making a pharmaceutical composition according to claim 7 comprising:
mixing the dihydropyrimidinone derivative under sterile conditions with the pharmaceutically acceptable carrier to form a mixture; and
providing the mixture in a unit dosage form.

11. A method of treating an ulcer, comprising:
administering to a patient in need thereof a therapeutically effective amount of the pharmaceutical composition according to claim 7.

12. The method of claim 11, wherein the composition is administered orally, nasally, rectally, parenterally, intracisternally, intra-vaginally, intraperitoneally, topically, transdermally, or by surgical implantation.

13. The method of claim 11, wherein the composition is administered in a form selected from the group consisting of liquid oral preparations, solid oral preparations, parenteral preparations, injectable suspensions, and liposomes.

14. A method of making a dihydropyrimidinone derivative, comprising:
refluxing 1-[4-(piperidin-1-yl) phenyl] ethan-1-one with dimethylforamide dimethylacetal (DMF-DMA) to obtain enaminone; and
refluxing a solution of enaminone, substituted benzaldehyde, urea, and Glacial acetic acid to yield a dihydropyrimidinone derivative having a structure of:

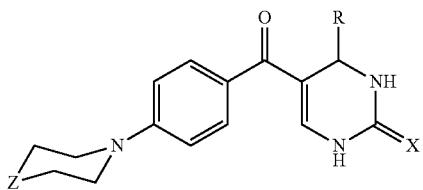

wherein
Z is selected from $CH_2$, O, and N;
X is selected from O and S; and
R represents an aryl, substituted aryl, heteroaryl, or substituted heteroaryl,
wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

15. The method of claim 14, wherein R is selected from the group consisting of 2-nitro phenyl, 3-nitro phenyl, 4-nitro phenyl, 4-chloro phenyl, 2,4-dichloro phenyl, 3,4-dimethoxy phenyl, 2-methoxy phenyl, 4-hydroxy phenyl, 3-hydroxy phenyl, dimethylamino phenyl, 3-methoxy phenyl, 4-ethoxy phenyl, 2,4,5-trimethoxy phenyl, 2,3,4-trimethoxy phenyl, 3,4,5-trimethoxy phenyl, 2,4,6-trimethoxy phenyl, and 2,4-dimethoxy phenyl.

16. The method of claim 14, wherein 1-[4-(piperidin-1-yl) phenyl] ethan-1-one is refluxed with dimethylforamide dimethylacetal (DMF-DMA) under a solvent free condition for about 10 hours.

17. The method of claim 14, wherein the solution of enaminone, substituted benzaldehyde, urea, and Glacial acetic acid is refluxed for about 3 hours.

18. The method of claim 14, further comprising:
recrystallizing the dihydropyrimidinone derivative from an ethanol and Glacial acetic acid mixture.

* * * * *